US012653773B2

(12) United States Patent
Shi et al.

(10) Patent No.: US 12,653,773 B2
(45) **Date of Patent: *Jun. 16, 2026**

(54) ORAL CARE COMPOSITIONS COMPRISING HOPS BETA ACID AND AMINO ACID

(71) Applicant: The Procter & Gamble Company, Cincinnati, OH (US)

(72) Inventors: Yunming Shi, Beijing (CN); Samuel James St. John, Cincinnati, OH (US); Ross Strand, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/418,609

(22) Filed: Jan. 22, 2024

(65) Prior Publication Data

US 2024/0156715 A1 May 16, 2024

Related U.S. Application Data

(63) Continuation of application No. 17/116,389, filed on Dec. 9, 2020, now Pat. No. 11,918,681, which is a continuation of application No. PCT/CN2020/119144, filed on Sep. 30, 2020.

(30) Foreign Application Priority Data

Sep. 30, 2019 (WO) ................ PCT/CN2019/109392

(51) Int. Cl.

| | |
|---|---|
| ***A61K 8/9789*** | (2017.01) |
| ***A61K 8/19*** | (2006.01) |
| ***A61K 8/20*** | (2006.01) |
| ***A61K 8/21*** | (2006.01) |
| ***A61K 8/27*** | (2006.01) |
| ***A61K 8/35*** | (2006.01) |
| ***A61K 8/44*** | (2006.01) |
| ***A61Q 11/00*** | (2006.01) |

(52) U.S. Cl.

CPC .............. *A61K 8/9789* (2017.08); *A61K 8/19* (2013.01); *A61K 8/20* (2013.01); *A61K 8/21* (2013.01); *A61K 8/27* (2013.01); *A61K 8/35* (2013.01); *A61K 8/44* (2013.01); *A61Q 11/00* (2013.01); *A61K 2800/30* (2013.01)

(58) Field of Classification Search

CPC ... A61K 8/81; A61K 8/21; A61K 8/27; A61K 8/19

USPC .................................................... 424/49, 401

See application file for complete search history.

(56) References Cited

U.S. PATENT DOCUMENTS

| | | | |
|---|---|---|---|
| 2,723,217 | A | 11/1955 | Gershon |
| 3,431,339 | A | 3/1969 | Gyarmathy et al. |
| 3,471,613 | A | 10/1969 | Gagolski |
| 3,624,120 | A | 11/1971 | Yetter |
| 3,639,570 | A | 2/1972 | Grand |
| 3,914,404 | A | 10/1975 | Langer |
| 3,925,556 | A | 12/1975 | Bauman |
| 3,932,603 | A | 1/1976 | Haas |
| 3,953,605 | A | 4/1976 | Bauman |
| 3,956,479 | A | 5/1976 | Bauman |
| 3,985,869 | A | 10/1976 | Yoshimura |
| 4,022,880 | A | 5/1977 | Vinson |
| 4,042,680 | A | 8/1977 | Muhler |
| 4,048,299 | A | 9/1977 | Litchfield |
| 4,088,752 | A | 5/1978 | Muhlemann |
| 4,108,981 | A | 8/1978 | Muhler |
| 4,132,773 | A | 1/1979 | Best |
| 4,154,813 | A | 5/1979 | Kleinberg |
| 4,166,073 | A | 8/1979 | Bauman |
| 4,235,875 | A | 11/1980 | Abramo |
| 4,416,867 | A | 11/1983 | Ritchey et al. |
| 4,435,381 | A | 3/1984 | Flagg |
| 4,438,093 | A | 3/1984 | Shimada |
| 4,618,489 | A | 10/1986 | Pollock |
| 4,737,359 | A | 4/1988 | Eigen |
| 4,976,954 | A | 12/1990 | Kleber |
| 5,064,640 | A | 11/1991 | Kleber |
| 5,281,410 | A | 1/1994 | Lukacovic |
| 5,370,863 | A | 12/1994 | Barney |
| 5,525,330 | A | 6/1996 | Gaffar |
| 5,531,982 | A | 7/1996 | Gaffar |
| 5,534,243 | A | 7/1996 | Dixon, Jr. |
| 5,741,487 | A | 4/1998 | Asai |

(Continued)

FOREIGN PATENT DOCUMENTS

| | | | |
|---|---|---|---|
| CN | 101123943 | A | 2/2008 |
| CN | 102811698 | A | 12/2012 |

(Continued)

OTHER PUBLICATIONS

Knowde, "Hopsteiner Beta Bio 45%-Hops Extract-Anti-Microbial Agent." www.knowde.com>stores>hopsteiner>products. Published online Feb. 16, 2021 (Year: 2021).*

(Continued)

*Primary Examiner* — Walter E Webb

(74) *Attorney, Agent, or Firm* — John G. Powell; Elizabeth Conklin

(57) ABSTRACT

Oral care compositions with an anticaries or anticavity effect. Oral care compositions that have one or more hops beta acids, such as from an extract from a species in the *Humulus* family, and one or more amino acids. Oral care compositions having one or more amino acids and an extract from *Humulus lupulus*. Methods of use of the disclosed compositions to disrupt biofilm in the oral cavity of a patient in need of treatment.

20 Claims, 4 Drawing Sheets

(56) References Cited

U.S. PATENT DOCUMENTS

| | | | | |
|---|---|---|---|---|
| 5,762,911 | A | 6/1998 | Kleinberg | |
| 5,770,588 | A | 6/1998 | Mcnamara | |
| 5,961,958 | A | 10/1999 | Homola | |
| 6,129,907 | A | 10/2000 | Sreenivasan | |
| 6,136,298 | A | 10/2000 | Gaffar | |
| 6,165,447 | A | 12/2000 | Trivedi | |
| 6,180,599 | B1 | 1/2001 | Min | |
| 6,207,138 | B1 * | 3/2001 | Zhang .................... | A61K 8/64 424/49 |
| 6,241,974 | B1 | 6/2001 | White, Jr. et al. | |
| 6,471,946 | B1 | 10/2002 | Takatsuka et al. | |
| 6,475,537 | B1 | 11/2002 | King et al. | |
| 6,521,216 | B1 * | 2/2003 | Glandorf ................. | A61K 8/21 424/49 |
| 6,607,711 | B2 | 8/2003 | Pedersen | |
| 6,846,478 | B1 | 1/2005 | Doyle et al. | |
| 7,910,139 | B2 | 3/2011 | Bombardelli | |
| 7,910,140 | B2 | 3/2011 | Wilson | |
| 8,071,136 | B2 | 12/2011 | Kuhrts | |
| 8,283,135 | B2 | 10/2012 | Doyle | |
| 8,652,495 | B2 | 2/2014 | Porter | |
| 8,691,190 | B2 | 4/2014 | Haught | |
| 8,900,644 | B2 | 12/2014 | Trivedi | |
| 9,119,879 | B2 | 9/2015 | Du-thumm | |
| 9,192,589 | B2 | 11/2015 | Subramanyam | |
| 9,532,932 | B2 | 1/2017 | Prencipe | |
| 9,855,200 | B2 | 1/2018 | Campbell et al. | |
| 9,883,995 | B2 | 2/2018 | Prencipe | |
| 10,105,303 | B2 | 10/2018 | Pan | |
| 10,596,088 | B2 | 3/2020 | Strand | |
| 10,596,089 | B2 | 3/2020 | Strand | |
| 10,603,263 | B2 | 3/2020 | Strand | |
| 2003/0003059 | A1 | 1/2003 | Dana | |
| 2003/0003069 | A1 | 1/2003 | Carson et al. | |
| 2003/0095931 | A1 | 5/2003 | Stier | |
| 2003/0157145 | A1 | 8/2003 | Kalili | |
| 2003/0165442 | A1 | 9/2003 | Baig | |
| 2004/0037790 | A1 | 2/2004 | Watanabe | |
| 2004/0042978 | A1 | 3/2004 | Embro | |
| 2004/0057908 | A1 | 3/2004 | Bowen | |
| 2004/0175480 | A1 | 9/2004 | Seman et al. | |
| 2005/0025720 | A1 | 2/2005 | Bailey | |
| 2006/0127343 | A1 | 6/2006 | Bernard et al. | |
| 2006/0134020 | A1 | 6/2006 | Robinson et al. | |
| 2006/0134024 | A1 | 6/2006 | Trivedi et al. | |
| 2006/0198849 | A1 | 9/2006 | Paau | |
| 2007/0092456 | A1 | 4/2007 | Inaba | |
| 2007/0248549 | A1 | 10/2007 | Kuhrts | |
| 2008/0003186 | A1 | 1/2008 | Imai | |
| 2008/0193531 | A1 | 8/2008 | Hermelin | |
| 2008/0219964 | A1 | 9/2008 | Keefe et al. | |
| 2009/0186090 | A1 | 7/2009 | Zaidel | |
| 2009/0202450 | A1 | 8/2009 | Prencipe | |
| 2009/0202451 | A1 | 8/2009 | Prencipe | |
| 2010/0158840 | A1 | 6/2010 | Hiramoto | |
| 2010/0316580 | A1 | 12/2010 | Kohli | |
| 2010/0322987 | A1 | 12/2010 | Robinson | |
| 2010/0322988 | A1 | 12/2010 | Prencipe | |
| 2010/0330003 | A1 | 12/2010 | Robinson | |
| 2011/0039927 | A1 | 2/2011 | Madsen et al. | |
| 2011/0052509 | A1 | 3/2011 | Subramanyam | |
| 2012/0207676 | A1 | 8/2012 | Gruaz-guyon | |
| 2012/0237455 | A1 * | 9/2012 | Trivedi ................ | A61K 36/725 424/769 |
| 2012/0237456 | A1 | 9/2012 | Trivedi et al. | |
| 2012/0244086 | A1 | 9/2012 | Trivedi et al. | |
| 2012/0244087 | A1 | 9/2012 | Trivedi et al. | |
| 2013/0142736 | A1 | 6/2013 | Robinson | |
| 2013/0287709 | A1 | 10/2013 | Maloney | |
| 2015/0297477 | A1 | 10/2015 | Poth | |
| 2015/0297500 | A1 | 10/2015 | Robinson | |
| 2015/0306015 | A1 | 10/2015 | Lin et al. | |
| 2015/0313813 | A1 | 11/2015 | Rege | |
| 2015/0320654 | A1 | 11/2015 | Li et al. | |
| 2016/0250122 | A1 | 9/2016 | Lin et al. | |
| 2016/0324738 | A1 | 11/2016 | Baig | |
| 2016/0324741 | A1 | 11/2016 | Baig | |
| 2017/0020801 | A1 | 1/2017 | Santarpia | |
| 2017/0056531 | A1 | 3/2017 | Shi | |
| 2017/0100312 | A1 | 4/2017 | Prencipe | |
| 2017/0319444 | A1 | 11/2017 | Dehghan | |
| 2017/0348206 | A1 | 12/2017 | Vemishetti | |
| 2017/0348550 | A1 | 12/2017 | Josias | |
| 2017/0367947 | A1 | 12/2017 | Rege et al. | |
| 2018/0028417 | A1 | 2/2018 | Koo | |
| 2018/0028423 | A1 | 2/2018 | Thomson et al. | |
| 2018/0072944 | A1 | 3/2018 | Shi | |
| 2018/0168960 | A1 | 6/2018 | Manus et al. | |
| 2019/0175466 | A1 | 6/2019 | Fei et al. | |
| 2019/0298620 | A1 | 10/2019 | Strand | |
| 2019/0298634 | A1 | 10/2019 | Strand | |
| 2019/0298635 | A1 | 10/2019 | Strand | |
| 2019/0298636 | A1 | 10/2019 | Strand | |
| 2021/0093525 | A1 | 4/2021 | Baig et al. | |
| 2021/0093528 | A1 | 4/2021 | St. John et al. | |
| 2021/0093549 | A1 | 4/2021 | Baig et al. | |
| 2021/0093550 | A1 | 4/2021 | Baig et al. | |
| 2021/0093551 | A1 | 4/2021 | Baig et al. | |
| 2021/0121392 | A1 | 4/2021 | Shi et al. | |
| 2022/0304918 | A1 | 9/2022 | Baig et al. | |
| 2022/0304919 | A1 | 9/2022 | St. John | |
| 2022/0313595 | A1 | 10/2022 | Baig et al. | |
| 2023/0293401 | A1 | 9/2023 | Baig | |
| 2023/0310287 | A1 | 10/2023 | Baig | |

FOREIGN PATENT DOCUMENTS

| | | | | |
|---|---|---|---|---|
| CN | 106075545 | A | 6/2016 | |
| CN | 106029175 | A | 10/2016 | |
| CN | 106309215 | A | 1/2017 | |
| CN | 106309629 | A | 1/2017 | |
| CN | 106389138 | A | 2/2017 | |
| CN | 106937921 | A | 7/2017 | |
| CN | 107468587 | A | 12/2017 | |
| CN | 108938544 | A | 12/2018 | |
| EP | 0311260 | B1 | 12/1994 | |
| EP | 0740932 | B1 | 9/2002 | |
| EP | 1185237 | B1 | 9/2003 | |
| EP | 1200053 | B1 | 12/2005 | |
| EP | 1203575 | B1 | 9/2010 | |
| EP | 1843741 | B1 | 4/2013 | |
| EP | 2753292 | B1 | 6/2018 | |
| GB | 1130566 | A | 10/1968 | |
| JP | S5326331 | A | 3/1978 | |
| JP | S63211219 | A | 9/1988 | |
| JP | 2001504083 | A | 3/2001 | |
| JP | 2001258502 | A | 9/2001 | |
| JP | 2008143870 | A | 6/2008 | |
| JP | 2009514789 | A | 4/2009 | |
| JP | 4347161 | B2 | 7/2009 | |
| JP | 2011063556 | A | 3/2011 | |
| JP | 2011088939 | A | 5/2011 | |
| JP | 2013512905 | A | 4/2013 | |
| JP | 2013523730 | A | 6/2013 | |
| JP | 2014221781 | A | 11/2014 | |
| JP | 2015521604 | A | 7/2015 | |
| JP | 2015155438 | A | 8/2015 | |
| JP | 2016516777 | A | 6/2016 | |
| JP | 2018091028 | A | 6/2018 | |
| JP | 2019052186 | A | 4/2019 | |
| KR | 20110133194 | A | 12/2011 | |
| WO | 9107163 | A1 | 5/1991 | |
| WO | 9909842 | A1 | 3/1999 | |
| WO | 0110401 | A1 | 2/2001 | |
| WO | 2006027248 | A2 | 3/2006 | |
| WO | 2006040189 | A1 | 4/2006 | |
| WO | 2007012080 | A3 | 5/2007 | |
| WO | 2007061796 | A2 | 5/2007 | |
| WO | 2008041055 | A1 | 4/2008 | |
| WO | 2008065875 | A1 | 6/2008 | |
| WO | 2011053291 | A1 | 5/2011 | |
| WO | WO-2012057739 | A1 * | 5/2012 | ............ A61Q 11/00 |
| WO | 2012087288 | A2 | 6/2012 | |
| WO | 2015171836 | A1 | 11/2015 | |

(56) References Cited

FOREIGN PATENT DOCUMENTS

| | | | |
|---|---|---|---|
| WO | 2015171837 | A1 | 11/2015 |
| WO | 2019183888 | A1 | 10/2019 |
| WO | 2022067140 | A1 | 3/2022 |
| WO | 2022067141 | A1 | 3/2022 |
| WO | 2022067142 | A1 | 3/2022 |

OTHER PUBLICATIONS

Wang et al., "Glycine inhibits the LPS-induced increase in cytosolic Ca2+ concentration and TNFa production in cardiomyocytes by activationg a glycine receptor." Acta Pharmacologica Sinica (2009) 30: 1107-1114. (Year: 2009).*

Harris, G., "Amino Acids and Peptides of Hops and Wort: I. Techniques and new compounds.", Journal of the Institute of Brewing, vol. 58, 1952, pp. 417-428.

Spirit Dental, "A Step-by-Step Guide to Proper Teeth Brushing.", Online retrieved from https://spiritdental.com/blog/categories/dental-health/a-step-by-step-guide-to-proper-teeth-brushing; dated Jul. 18, 2019, 02 Pages.

All Office Actions; U.S. Appl. No. 18/655,468, filed May 6, 2024.

Unpublished U.S. Appl. No. 18/655,468, filed May 6, 2024, to Arif Ali Baig et. al.

"BetaBio 45%", Retrieved from the Internet: URL:https://www.hopsteiner.com/wp-content/uploads/2019/07/25_09_BetaBio-45.pdf; Jul. 1, 2019, 3 pages.

"GNPD—Maximum Bio-Active Super Fresh Toothpaste", Mar. 1, 2014, XP0551 86450, Retrieved from the Internet: URL: http://www.gnpd.com/sinatra/recordpage/2337697/from_search/IQ5ZuZM2pG/, 2 Pages.

Oral Care, Honeywell Fine Chemicals, Retrieved from URL: https://www.additiveschemicals-honeywell.com/finechemicals/applications/personal-care/oral-care/, Nov. 30, 2020, pp. 1-3.

PCT Search Report and Written Opinion for PCT/CN2019/109392 dated Jun. 23, 2020, 8 pages.

PCT Search Report and Written Opinion for PCT/CN2020/119144 dated Dec. 23, 2021, 12 pages.

Akande, O.O. et al., "A Laboratory Evaluation of the Efficacy of a Herbal Dentifrice on Dental Caries in the Rat", African J of Bio Res, vol. 7, 2004, pp. 89-92.

All Office Actions; U.S. Appl. No. 17/037,766, filed Sep. 30, 2020.

All Office Actions; U.S. Appl. No. 17/037,773, filed Sep. 30, 2020.

All Office Actions; U.S. Appl. No. 17/037,776, filed Sep. 30, 2020.

All Office Actions; U.S. Appl. No. 17/037,780, filed Sep. 30, 2020.

All Office Actions; U.S. Appl. No. 17/037,789, filed Sep. 30, 2020.

All Office Actions; U.S. Appl. No. 17/116,389, filed Dec. 9, 2020.

All Office Actions; U.S. Appl. No. 17/704,023, filed Mar. 25, 2022.

All Office Actions; U.S. Appl. No. 17/704,027, filed Mar. 25, 2022.

All Office Actions; U.S. Appl. No. 17/704,028, filed Mar. 25, 2022.

All Office Actions; U.S. Appl. No. 18/322,652, filed May 24, 2023.

All Office Actions; U.S. Appl. No. 18/322,979, filed May 24, 2023.

Anbar, M. et al. "Organic Polymeric Polyphosphonates as Potential Preventive Agents of Dental Caries: In Vivo Experiments", J. Dent Res, vol. 53(5), 1974, pp. 1240-1244.

Barth Haas Isohop technical data sheet, Rev. 7, approved on Jul. 4, 2022, 3 pages.

Bhattacharya et al., "Inhibition of *Streptococcus* Mutans and Other Oral Streptococci by Hop (Humulus Lupulus L.) Constituents", Economic Botany, vol. 57, No. 1, Jan. 2003, pp. 118-125.

Colgate, "What are the Signs and Symptoms of Gingivitis?", Online retrieved from ""https://www.colgate.com/en-us/oral-health/gum-disease/what-is-gingivitis-signs-and-symptoms" target="_blank"https://www.colgate.com/en-us/oral-health/gum-disease/what-is-gingivitis-signs-and-symptoms/a", Jul. 14, 2021, 8 Pages.

Comprehensive Separation and Structural Analyses of Polyphenols and Related Compounds from Bracts of Hops, XP 55753130A1 Journal of Agricultural and food chemistry, Yoshihisa Tanaka, Year, 2014, pp. 2198-2206.

Database GNPD [Online] Mintel, anonymous: "Regular Mouth Wash", XP055753124, Retrieved from www.gnpd.com, Database accession No. 10441104 abstract, Feb. 5, 2009, pp. 1-3.

Database GNPD [Online] Mintel, anonymous: "Strawberry Milk Flavoured Anti-Cavity Toothpaste for Kids", XP055755176, Database accession No. 4757005; Apr. 18, 2017, p. 1-3.

Database GNPD [Online] Mintel, anonymous: "Whitening Tooth Powder", XP055755184, Database accession No. 1777364 abstract, Apr. 23, 2012, pp. 1-4.

Database GNPD [Online] Miintel, anonymous: "Daily Toothpaste!", XP055755179, Database accession No. 3287031 Abstract, Jul. 14, 2015, pp. 1-3.

Database WPI, Week 201807, Feb. 1, 2008 (Feb. 1, 2008), Thomson Scientific, London, GB; AN 2017-88895Q XP002801332, & CN 107485599 A (Univ Southwest) Dec. 19, 2017 (Dec. 19, 2017) abstract.

Gaffar, Abdul et al. "Effects of EDITEMPA on Dental Calculus and Caries Formation in Vivo", Calcif Tissue Int 35, 1983, pp. 362-365.

Hopsteiner Store, XP 93067800A1, Consent to Cookies & Data processing, URL Link; https;//lwww.hopsteiner-shopde/en/about-hopsteiner, No Known Date, 3 pgs.

Hopsteiner, Beta Bio45%, XP55753265A1, No Known date, 3 pgs.

Jason Tetro, "The Secret to Better Teeth Found in Beer Breweries", Under the Microscope, Retrieved from the Internet: URL: https://www.popsci.com/blog-network/under-microscope/secret-better-teeth-found-beer-breweries/, Mar. 11, 2014, pp. 1-9.

Mckenna Francine: "German Inventions in Everyday Use", XP055773018, Retrieved from the Internet: URL:https://www.germanpulse.com/2012/05/08/german-inventions-in-everyday-use/ [retrieved on Feb. 5, 2021] the whole document ; Jan. 1, 2012, 3 pages.

Muhlemann, HR et al. "Reduction of Plaque and Gingivitis by Stannous Fluoride Stabilized with Amine Fluoride", Caries Research 15:2 , 1981,1 page.

Roger Stevens, "The Chemistry of Hop Constituents", Brewing Industry Research Foundation, Mar. 31, 1966, pp. 19-71.

Rotgans, J et al. "The Effect of Brushing with a Toothpaste Containing Amyloglucosidase and Glucose Oxidase on Dental Caries in Rats", Caries Res. 13, 1979, pp. 150-153.

Sharma, Siddharth et al. "Laboratory Evaluation of the Efficacy of Formulated Polyherbal Toothpaste "Oralis S" on Dental Caries in Rats", IJPRAS, vol. 3(2), 2014, pp. 47-50.

Simpson et al., "Factors Affecting Antibacterial Activity of Hop Compounds and Their Derivatives", Journal of Applied Bacteriology, vol. 72, 1992, pp. 327-334.

Spiritdental.com_ A Step-by-Step Guide to Proper Teeth Brushing, "www.spiritdental.com", Published online Jul. 18, 2019, 5 Pages.

Stookey, G. K. et al. "Animal Caries Models for Evaluating Fluoride Dentifrices" Adv. Dent. Res 9(3), Nov. 1995, pp. 198-207.

Sullivan, RJ et al. "Development of an enhanced anticaries efficacy dual component dentifrice containing sodium fluoride and dicalcium phosphate dihydrate" Am J. Dent , 14 Spec No. 3A-11A, May 2001, pp. 1-2.

Xiang, et al., "Penetration and Bactericidal Efficacy of Two Oral Care Products in an Oral Biofilm Model", Am J Dent, vol. 31, Issue1, Feb. 2018, 07 pages.

Yang et al. "Relation between chemotaxis and consumption of amino acids in bacteria", Molecular Microbiology 96, 2015, pp. 1272-1282.

All Office Actions; U.S. Appl. No. 18/788,266, filed Jul. 30, 2024.

Unpublished U.S. Appl. No. 18/788,266, filed Jul. 30, 2024, to Arif Ali Baig et al.

PCT Search Report and Written Opinion for PCT/CN2020/119144 dated Dec. 31, 2020; 11 pages.

Agarwal et al., "Prevention of Dental Caries-Measures beyond Fluoride.", In Journal of Oral Hygiene & Health, vol. 2, Issue 1, Mar. 3, 2014, 6 Pages.

All Office Actions: U.S. Appl. No. 19/230,165, filed Jun. 6, 2025.

Bogdanova et al. "Antibiofilm activity of bioactive hop compounds humulone, lupulone and xanthohumol toward susceptible and resistant staphylococci", Research in Microbiology Journal, vol. 169, Issue 3, Apr. 2018, pp. 127-134.

(56) References Cited

OTHER PUBLICATIONS

Meyer et al. "Quantifying Drug Combination Synergy along Potency and Efficacy Axes", Retrieved from Internet: https://pubmed.ncbi.nim.nih.gov/30797775/, Feb. 27, 2019, 46 Pages.
Unpublished U.S. Appl. No. 19/230,165, filed Jun. 6, 2025, to Arif Ali Baig et al.

* cited by examiner

ORAL CARE COMPOSITIONS COMPRISING HOPS BETA ACID AND AMINO ACID

FIELD OF THE INVENTION

The present invention is directed to compositions with improved anticaries and/or antibacterial activity. The present invention is also directed to compositions comprising one or more hops beta acids, such from an extract from *Humulus lupulus*, and one or more amino acids, such as glycine.

BACKGROUND OF THE INVENTION

Oral care compositions, such as toothpaste and/or dentifrice compositions, can be applied to the oral cavity to clean and/or maintain the aesthetics and/or health of the teeth, gums, and/or tongue. Additionally, many oral care compositions are used to deliver active ingredients directly to oral care surfaces. However, it can be challenging to deliver active ingredients to biofilm.

Biofilm is a collective of one or more types of microorganisms that can grow on many different surfaces. One common example of a biofilm is dental plaque, which is a buildup of bacteria that forms on surfaces within the oral cavity.

Initially, dental plaque is a colorless deposit, but once it forms tartar, it is often brown or pale yellow. Tartar is a hard-calcified deposit that forms by precipitation of minerals into the biofilm, which serves as a roughened surface that can host additional biofilm formation. This is known as calculus buildup. Calculus formation is associated with a number of clinical manifestations, including bad breath, receding gums and chronically inflamed gingiva. Brushing and flossing can remove plaque from which calculus forms; however, once formed, calculus is too firmly attached to be removed with a toothbrush as dental plaque biofilm communities are extremely recalcitrant to external chemical and physical perturbations.

As such, there is a need for oral care compositions which can penetrate the biofilm to deliver active agents.

SUMMARY OF THE INVENTION

Disclosed herein is an oral care composition comprising: (a) from about 0.01% to about 10%, by weight of the composition, of hops beta acid; and (b) from about 0.01% to about 10%, by weight of the composition, of amino acid.

Also disclosed herein is a method of disrupting a dental biofilm in the oral cavity of a patient having dental biofilm in the oral cavity comprising applying an oral care composition to the dental biofilm, wherein the oral care composition comprises: (a) from about 0.01% to about 10%, by weight of the composition, of hops beta acid, and (b) from about 0.01% to about 10%, by weight of the composition, of amino acid.

DETAILED DESCRIPTION OF THE INVENTION

Figure 1:
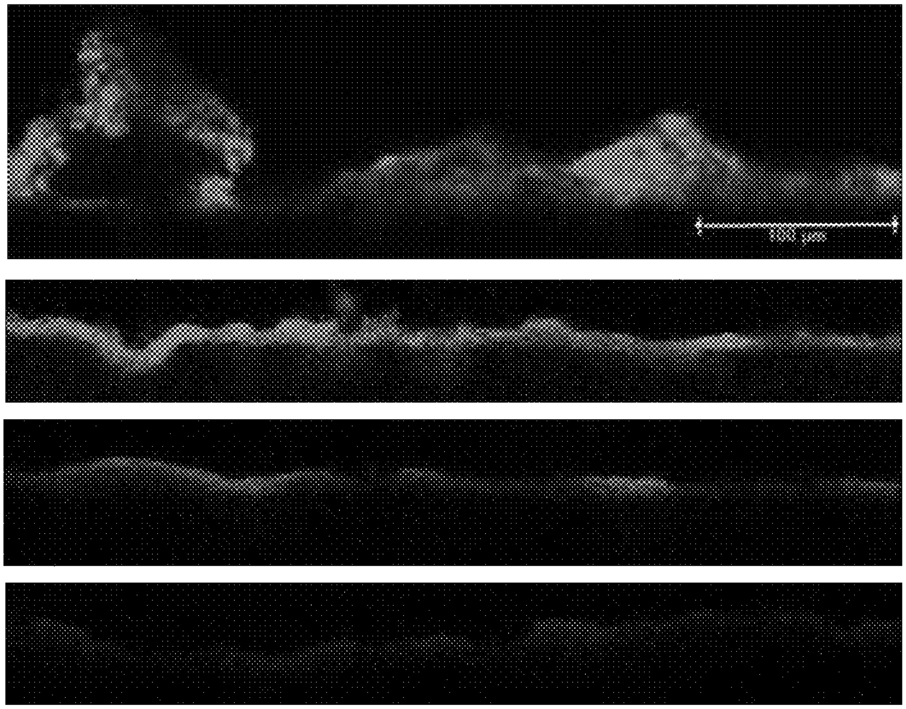
FIG. 1 shows a photograph of the EPS thickness of in situ biofilm treated with (top to bottom) Ex. 1, Ex. 2, Ex. 3, and Ex. 4.

The present invention is directed to oral care compositions that can penetrate, disrupt, and/or destabilize dental biofilm. Additionally, the present invention is directed to oral care compositions comprising one or more hops beta acids and an amino acid. The disclosed compositions can lead to the disruption and/or destabilization of the dental biofilm architecture achieved through the use of an amino acid, such as glycine. Further, the destabilized biofilm allows for improved penetration of ingredients to modulate the bacterial metabolites and toxins, as seen in the enhances stannous penetration and neutralization of the LPS with the addition of glycine. While not wishing to be being bound by theory, it is believed that the effect in altering the biofilm architecture can result in a reduction in the thickness of the biofilm which, can reduce the amount and effects of bacteria and their metabolites.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

The term "oral care composition", as used herein, includes a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, toothpaste, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "orally acceptable carrier" comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a bleaching agent."

All measurements referred to herein are made at about 23° C. (i.e. room temperature) unless otherwise specified.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, and so forth.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The oral care composition can be in any suitable form, such as a solid, liquid, powder, paste, or combinations thereof. The oral care composition can be dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The components of the dentifrice composition can be incorporated into a film, a strip, a foam, or a fiber-based dentifrice composition. The oral care composition can include a variety of active and inactive ingredients, such as, for example, but not limited to a hops extract, a tin ion source, a calcium ion source, water, a fluoride ion source, zinc ion source, one or more polyphosphates, humectants, surfactants, other ingredients, and the like, as well as any combination thereof, as described below.

Section headers are provided below for organization and convenience only. The section headers do not suggest that a compound cannot be within more than one section. In fact, compounds can fall within more than one section. For example, stannous chloride can be both a tin ion source and a biofilm modifier, stannous fluoride can be both a tin ion source and a fluoride ion source, glycine can be an amino acid, a buffering agent, and/or a biofilm modifier, among numerous other compounds that can fit amongst several categories and/or sections.

*Humulus Lupulus*

The oral care compositions of the present invention comprise at least one hops compound from Formula I and/or Formula IV. The compound from Formula I and/or Formula IV can be provided by any suitable source, such as an extract from *Humulus lupulus* or Hops, *Humulus lupulus* itself, a synthetically derived compound, and/or salts, prodrugs, or other analogs thereof. The hops extract can comprise one or more hops alpha acids, one or more hops iso-alpha acids, one or more hops beta acids, one or more hops oils, one or more flavonoids, one or more solvents, and/or water. Suitable hops alpha acids (generically shown in Formula I) can include humulone (Formula II), adhumulone, cohumulone, posthumulone, prehumulone, and/or mixtures thereof. Suitable hops iso-alpha acids can include cis-isohumulone and/or trans-isohumulone. The isomerization of humulone into trans-isohumulone can be represented by Formula III.

Formula I

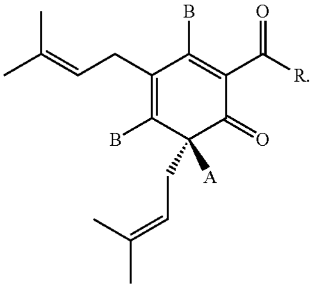

Hops Alpha Acids. A is the acidic hydroxyl functional group in the alpha position, B are the acidic hydroxyl functional groups in the beta position, and R is an alkyl functional group.

Formula II

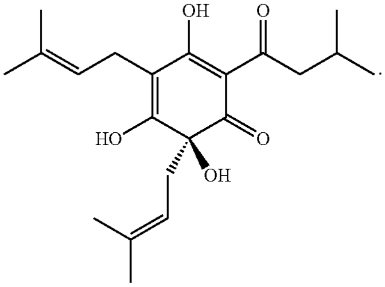

Humulone

-continued

Formula III

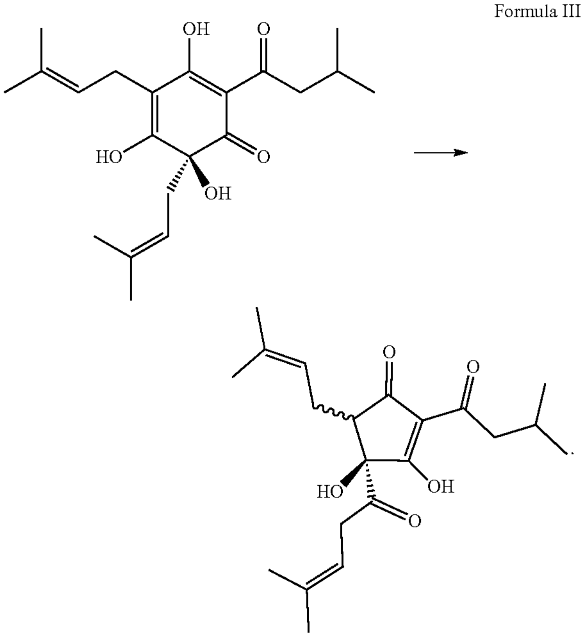

Isomerization of Humulone to isohumulone.

Suitable hops beta acids can include lupulone, adlupulone, colupulone, and/or mixtures thereof. A suitable hops beta acid can include a compound a described in Formula IV, V, VI, and/or VII.

Formula IV

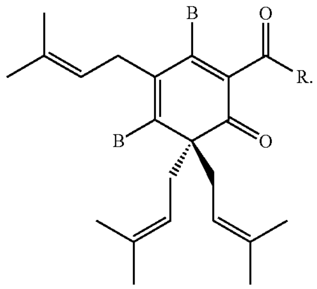

Hops Beta Acids. B are the acidic hydroxyl functional groups in the beta position and R is an alkyl functional group.

Formula V

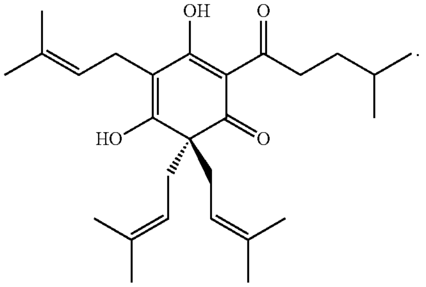

Lupulone

-continued

Formula VI

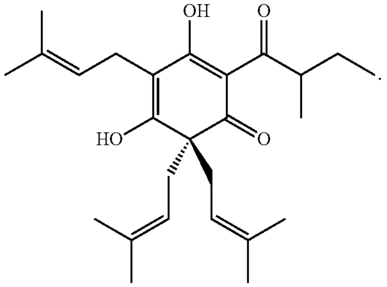

Adlupulone

Formula VII

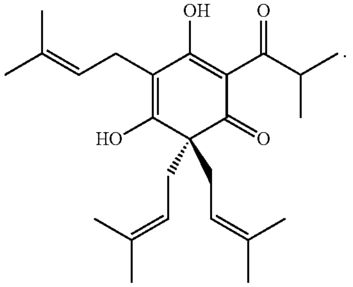

Colupulone

While hops alpha acids can demonstrate some antibacterial activity, hops alpha acids also have a bitter taste. The bitterness provided by hops alpha acids can be suitable for beer, but are not suitable for use in oral care compositions. In contrast, hops beta acids can be associated with a higher antibacterial and/or anticaries activity, but not as bitter a taste. Thus, a hops extract with a higher proportion of beta acids to alpha acids than normally found in nature, can be suitable for use in oral care compositions for use as an antibacterial and/or anticaries agent.

A natural hops source can comprise from about 2% to about 12%, by weight of the hops source, of hops beta acids depending on the variety of hops. Hops extracts used in other contexts, such as in the brewing of beer, can comprise from about 15% to about 35%, by weight of the extract, of hops beta acids. The hops extract desired herein can comprise at least about 35%, at least about 40%, at least about 45%, from about 35% to about 95%, from about 40% to about 90%, or from about 45% to about 99%, of hops beta acids. The hops beta acids can be in an acidic form (i.e. with attached hydrogen atom(s) to the hydroxyl functional group(s)) or as a salt form.

A suitable hops extract is described in detail in U.S. Pat. No. 7,910,140, which is herein incorporated by reference in its entirety. The hops beta acids desired can be non-hydrogenated, partially hydrogenated by a non-naturally occurring chemical reaction, or hydrogenated by a non-naturally occurring chemical reaction. The hops beta acid can be essentially free of or substantially free of hydrogenated hops beta acid and/or hops acid. A non-naturally occurring chemical reaction is a chemical reaction that was conducted with the aid of chemical compound not found within *Humulus lupulus*, such as a chemical hydrogenation reaction conducted with high heat not normally experienced by *Humulus lupulus* in the wild and/or a metal catalyst.

A natural hops source can comprise from about 2% to about 12%, by weight of the hops source, of hops alpha acids. Hops extracts used in other contexts, such as in the brewing of beer, can comprise from about 15% to about 35%, by weight of the extract, of hops alpha acids. The hops extract desired herein can comprise less than about 10%, less than about 5%, less than about 1%, or less than about 0.5%, by weight of the extract, of hops alpha acids.

Hops oils can include terpene hydrocarbons, such as myrcene, humulene, caryophyllene, and/or mixtures thereof. The hops extract desired herein can comprise less than 5%, less than 2.5%, or less than 2%, by weight of the extract, of one or more hops oils.

Flavonoids present in the hops extract can include xanthohumol, 8-prenylnaringenin, isoxanthohumol, and/or mixtures thereof. The hops extract can be substantially free of, essentially free of, or have less than 250 ppm, less than 150 ppm, and/or less than 100 ppm of one or more flavonoids.

As described in U.S. Pat. No. 5,370,863, hops acids have been previously added to oral care compositions. However, the oral care compositions taught by U.S. Pat. No. 5,370,863 only included up to 0.01%, by weight of the oral care composition. While not wishing to be bound by theory, it is believed that U.S. Pat. No. 5,370,863 could only incorporate a low amount of hops acids because of the bitterness of hops alpha acids. A hops extract with a low level of hops alpha acids would not have this concern.

The hops compound can be combined with or free from an extract from another plant, such as a species from genus *Magnolia*. The hops compounds can be combined with or free from triclosan.

The oral care composition can comprise from about 0.01% to about 10%, greater than 0.01% to about 10%, from about 0.05%, to about 10%, from about 0.1% to about 10%, from about 0.2% to about 10%, from about 0.2% to about 10%, from about 0.2% to about 5%, from about 0.25% to about 2%, from about 0.05% to about 2%, or from greater than 0.25% to about 2%, of hops beta acid, as described herein. The hops beta acids can be provided by a suitable hops extract, the hops plant itself, or a synthetically derived compound. The hops beta acid can be provided as neutral, acidic compounds, and/or as salts with a suitable counter ion, such as sodium, potassium, ammonia, or any other suitable counter ion.

The hops beta acid can be provided by a hops extract, such as an extract from *Humulus lupulus* with at least 35%, by weight of the extract, of hops beta acid and less than 1%, by weight of the hops extract, of hops alpha acid. The oral care composition can comprise 0.01% to about 10%, greater than 0.01% to about 10%, from about 0.05%, to about 10%, from about 0.1% to about 10%, from about 0.2% to about 10%, from about 0.2% to about 10%, from about 0.2% to about 5%, from about 0.25% to about 2%, from about 0.05% to about 2%, or from greater than 0.25% to about 2%, of hops extract, as described herein.

Amino Acid

The oral care composition can comprise one or more amino acids. The disclosed compositions can lead to the disruption and/or destabilization of the dental biofilm architecture achieved through the use of an amino acid, such as glycine. Further, the destabilized biofilm allows for improved penetration of ingredients to modulate the bacterial metabolites and toxins, as seen in the enhances stannous penetration and neutralization of the LPS with the addition of glycine. While not wishing to be being bound by theory, it is believed that the effect in altering the biofilm architecture can result in a reduction in the thickness of the biofilm which, can reduce the amount and effects of bacteria and their metabolites.

Amino acids are organic compounds that contain an amine functional group, a carboxyl functional group, and a side chain specific to each amino acid. Suitable amino acids include, for example, amino acids with a positive or negative side chain, amino acids with an acidic or basic side chain, amino acids with polar uncharged side chains, amino acids with hydrophobic side chains, and/or combinations thereof. Suitable amino acids also include, for example, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, citrulline, ornithine, creatine, diaminobutonic acid, diaminoproprionic acid, salts thereof, and/or combinations thereof.

Suitable amino acids include one or more basic amino acids, one or more acidic amino acids, one or more neutral amino acids, or combinations thereof.

The oral care composition can comprise from about 0.01% to about 20%, from about 0.1% to about 10%, from about 0.5% to about 6%, or from about 1% to about 10% of amino acid, by weight of the oral care composition.

Fluoride Ion Source

The oral care composition can comprise fluoride, such as from a fluoride ion source. The fluoride ion source can comprise one or more fluoride containing compounds, such as stannous fluoride, sodium fluoride, titanium fluoride, calcium fluoride, calcium phosphate silicate fluoride, potassium fluoride, amine fluoride, sodium monofluorophosphate, zinc fluoride, and/or mixtures thereof.

The fluoride ion source and the tin ion source can be the same compound, such as for example, stannous fluoride, which can generate tin ions and fluoride ions. Additionally, the fluoride ion source and the tin ion source can be separate compounds, such as when the tin ion source is stannous chloride and the fluoride ion source is sodium monofluorophosphate or sodium fluoride.

The fluoride ion source and the zinc ion source can be the same compound, such as for example, zinc fluoride, which can generate zinc ions and fluoride ions. Additionally, the fluoride ion source and the zinc ion source can be separate compounds, such as when the zinc ion source is zinc phosphate and the fluoride ion source is stannous fluoride.

The fluoride ion source can be essentially free of, substantially free of, or free of stannous fluoride. Thus, the oral care composition can comprise sodium fluoride, potassium fluoride, amine fluoride, sodium monofluorophosphate, zinc fluoride, and/or mixtures thereof.

The oral care composition can comprise a fluoride ion source capable of providing from about 50 ppm to about 5000 ppm, and preferably from about 500 ppm to about 3000 ppm of free fluoride ions. To deliver the desired amount of fluoride ions, the fluoride ion source may be present in the oral care composition at an amount of from about 0.0025% to about 5%, from about 0.01% to about 10%, from about 0.2% to about 1%, from about 0.5% to about 1.5%, or from about 0.3% to about 0.6%, by weight of the oral care composition. Alternatively, the oral care composition can comprise less than 0.1%, less than 0.01%, be essentially free of, substantially free of, or free of a fluoride ion source.

Tin Ion Source

The oral care composition of the present invention can comprise tin, such as from a tin ion source. The tin ion source can be any suitable compound that can provide tin ions in an oral care composition and/or deliver tin ions to the oral cavity when the dentifrice composition is applied to the oral cavity. The tin ion source can comprise one or more tin containing compounds, such as stannous fluoride, stannous chloride, stannous bromide, stannous iodide, stannous oxide, stannous oxalate, stannous sulfate, stannous sulfide, stannic fluoride, stannic chloride, stannic bromide, stannic iodide, stannic sulfide, and/or mixtures thereof. Tin ion source can comprise stannous fluoride, stannous chloride, and/or mixture thereof. The tin ion source can also be a fluoride-free tin ion source, such as stannous chloride.

The oral care composition can comprise from about 0.0025% to about 5%, from about 0.01% to about 10%, from about 0.2% to about 1%, from about 0.5% to about 1.5%, or from about 0.3% to about 0.6%, by weight of the oral care composition, of a tin ion source.

Ca Ion Source

The oral care composition of the present invention can comprise calcium, such as from a calcium ion source. The calcium ion source can be any suitable compound or molecule that can provide calcium ions in an oral care composition and/or deliver calcium ions to the oral cavity when the oral care composition is applied to the oral cavity. The calcium ion source can comprise a calcium salt, a calcium abrasive, and/or combinations thereof. In some cases, a calcium salt may also be considered a calcium abrasive or a calcium abrasive may also be considered a calcium salt.

The calcium ion source can comprise a calcium abrasive. The calcium abrasive can be any suitable abrasive compound that can provide calcium ions in an oral care composition and/or deliver calcium ions to the oral cavity when the oral care composition is applied to the oral cavity. The calcium abrasive can comprise one or more calcium abrasive compounds, such as calcium carbonate, precipitated calcium carbonate (PCC), ground calcium carbonate (GCC), chalk, dicalcium phosphate, calcium pyrophosphate, and/or mixtures thereof.

The calcium ion source can comprise a calcium salt, or a compound that can provide calcium ions in an oral care composition and/or deliver calcium ions to the oral cavity when the oral care composition is applied to the oral cavity that can not act as an abrasive. The calcium salt can comprise one or more calcium compounds, such as calcium chloride, calcium nitrate, calcium phosphate, calcium lactate, calcium oxalate, calcium oxide, calcium gluconate, calcium citrate, calcium bromide, calcium iodate, calcium iodide, hydroxyapatite, fluorapatite, calcium sulfate, calcium glycerophosphate, and/or combinations thereof.

The oral care composition can comprise from about 5% to about 70%, from about 10% to about 50%, from about 10% to about 60%, from about 20% to about 50%, from about 25% to about 40%, or from about 1% to about 50% of a calcium ion source.

Buffering Agent

The oral care composition can comprise a buffering agent. The buffering agent can be a weak acid or base that can maintain a particular pH at a selected site in the oral cavity. For example, the buffering agent can maintain a pH at a tooth's surface to mitigate the impact of plaque acids produced by bacteria. The buffering agent can comprise a conjugate acid of an ion also present in the oral care composition. For example, if the calcium ion source comprises calcium carbonate, the buffering agent can comprise a bicarbonate anion ($-HCO_3^-$). The buffering agent can comprise a conjugate acid/base pair, such as citric acid and sodium citrate.

Suitable buffering systems can include phosphate, citrate salts, carbonate/bicarbonate salts, a tris buffer, imidazole, urea, borate, and/or combinations thereof. Suitable buffering agents include bicarbonate salts, such as sodium bicarbonate, glycine, orthophosphate, arginine, urea, and or/combinations thereof.

The oral care composition can comprise from about 1% to about 30%, from about 5% to about 25% or from about 10% to about 20%, of one or more buffering agents.

Biofilm Modifier

The oral care composition can comprise one or more biofilm modifiers. A biofilm modifier can comprise a polyol, an ammonia generating compound, and/or a glucosyltransferase inhibitor.

A polyol is an organic compound with more than one hydroxyl functional groups. The polyol can be any suitable compound that can weakly associate, interact, or bond to tin ions while the oral care composition is stored prior to use. The polyol can be a sugar alcohol, which area class of polyols that can be obtained through the hydrogenation of sugar compounds with the formula $(CHOH)_nH_2$. The polyol can be glycerin, erythritol, xylitol, sorbitol, mannitol, butylene glycol, lactitol, and/or combinations thereof. The oral care composition can comprise 0.01% to about 70%, from about 5% to about 70%, from about 5% to about 50%, from about 10% to about 60%, from about 10% to about 25%, or from about 20% to about 80%, by weight of the oral care composition, of a polyol.

The ammonia generating compound can be any suitable compound that can generate ammonia upon delivery to the oral cavity. Suitable ammonia generating compounds include arginine, urea, and/or combinations thereof. The oral care composition can comprise from about 0.01% to about 10%, from about 1% to about 5%, or from about 1% to about 25% of one or more ammonia generating compounds.

The glucosyltransferase inhibitor can be any suitable compound that can inhibit a glucosyltransferase. Glucosyltransferases are enzymes that can establish natural glycosidic linkages. In particular, these enzymes break down poly- or oligosaccharide moieties into simple sugars for bacteria associated with dental caries. As such, any compound that can inhibit this process can help prevent dental caries. Suitable glucosyltransferase inhibitors include oleic acid, epicatechin, tannins, tannic acid, moenomycin, caspofungin, ethambutol, lufenuron, and/or combinations thereof. The oral care composition can comprise from about 0.001% to about 5%, from about 0.01% to about 2%, or about 1% of one or more glucosyltransferase inhibitors.

Metal Ion Source

The oral care composition can comprise metal, such as from a metal ion source comprising one or more metal ions. The metal ion source can comprise or be in addition to the tin ion source and/or the zinc ion source, as described herein. Suitable metal ion sources include compounds with metal ions, such as, but not limited to Sn, Zn, Cu, Mn, Mg, Sr, Ti, Fe, Mo, B, Ba, Ce, Al, In and/or mixtures thereof. The trace metal source can be any compound with a suitable metal and any accompanying ligands and/or anions.

Suitable ligands and/or anions that can be paired with metal ion sources include, but are not limited to acetate, ammonium sulfate, benzoate, bromide, borate, carbonate, chloride, citrate, gluconate, glycerophosphate, hydroxide, iodide, oxide, propionate, D-lactate, DL-lactate, orthophosphate, pyrophosphate, sulfate, nitrate, tartrate, and/or mixtures thereof.

The oral care composition can comprise from about 0.01% to about 10%, from about 1% to about 5%, or from about 0.5% to about 15% of a metal ion source.

Antibacterial Agents

The oral care composition can comprise one or more antibacterial agents. Suitable antibacterial agents include any molecule that provides antibacterial activity in the oral cavity. Suitable antibacterial agents include hops acids, tin ion sources, benzyl alcohol, sodium benzoate, methylglycyl acetate, menthyl lactate, L-menthol, o-neomenthol, chlorophyllin copper complex, phenol, oxyquinoline, and/or combinations thereof.

The oral care composition can comprise from about 0.01% to about 10%, from about 1% to about 5%, or from about 0.5% to about 15% of an antibacterial agent.

Bioactive Materials

The oral care composition can also include bioactive materials suitable for the remineralization of a tooth. Suitable bioactive materials include bioactive glasses, Novamin™, Recaldent™, hydroxyapatite, one or more amino acids, such as, for example, arginine, citrulline, glycine, lysine, or histidine, or combinations thereof. Suitable examples of compositions comprising arginine are found in U.S. Pat. Nos. 4,154,813 and 5,762,911, which are herein incorporated by reference in their entirety. Other suitable bioactive materials include any calcium phosphate compound. Other suitable bioactive materials include compounds comprising a calcium source and a phosphate source.

Bioactive glasses are comprising calcium and/or phosphate which can be present in a proportion that is similar to hydroxyapatite. These glasses can bond to the tissue and are biocompatible. Bioactive glasses can include a phosphopeptide, a calcium source, phosphate source, a silica source, a sodium source, and/or combinations thereof.

The oral care composition can comprise from about 0.01% to about 20%, from about 0.1% to about 10%, or from about 1% to about 10% of a bioactive material by weight of the oral care composition.

Abrasive

The oral care composition can comprise a calcium abrasive, as described herein, and/or a non-calcium abrasive, such as bentonite, silica gel (by itself, and of any structure), precipitated silica, amorphous precipitated silica (by itself, and of any structure as well), hydrated silica, perlite, titanium dioxide, calcium pyrophosphate, dicalcium phosphate dihydrate, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the oral care compositions to tailor the polishing characteristics of the target dentifrice formulation. The oral care composition can comprise from about 5% to about 70%, from about 10% to about 50%, from about 10% to about 60%, from about 20% to about 50%, from about 25% to about 40%, or from about 1% to about 50%, by weight of the oral care composition, of the non-calcium abrasive.

Alternatively, the oral care composition can be substantially free of, essentially free of, or free of silica, alumina, or any other non-calcium abrasive. The oral care composition can comprise less than about 5%, less than about 1%, less than about 0.5%, less than about 0.1%, or 0% of a non-calcium abrasive, such as silica and/or alumina.

Water

The oral care composition of the present invention can be anhydrous, a low water formulation, or a high water formulation. In total, the oral care composition can comprise from 0% to about 99%, from about 5% to about 75%, about 20% or greater, about 30% or greater, or about 50% or greater by weight of the composition, of water. Preferably, the water is USP water.

In a high water oral care composition and/or toothpaste formulation, the oral care composition comprises from about 45% to about 75%, by weight of the composition, of water. The high water oral care composition and/or toothpaste formulation can comprise from about 45% to about 65%, from about 45% to about 55%, or from about 46% to about 54%, by weight of the composition, of water. The water may be added to the high water formulation and/or may come into the composition from the inclusion of other ingredients.

In a low water oral care composition and/or toothpaste formulation, the oral care composition comprises from about 5% to about 45%, by weight of the composition, of water. The low water oral care composition can comprise from about 5% to about 35%, from about 10% to about 25%, or from about 20% to about 25%, by weight of the composition, of water. The water may be added to the low water formulation and/or may come into the composition from the inclusion of other ingredients.

In an anhydrous oral care composition and/or toothpaste formulation, the oral care composition comprises less than about 10%, by weight of the composition, of water. The anhydrous composition comprises less than about 5%, less than about 1%, or 0%, by weight of the composition, of water. The water may be added to the anhydrous formulation and/or may come into the composition from the inclusion of other ingredients.

A mouth rinse formulation comprises from about 75% to about 99%, from about 75% to about 95%, or from about 80% to about 95% of water.

The composition can also comprise other orally acceptable carrier materials, such as alcohol, humectants, polymers, surfactants, and acceptance improving agents, such as flavoring, sweetening, coloring and/or cooling agents.

pH

The pH of the disclosed composition can be from about 4 to about 10, from about 7 to about 10, greater than 7 to about 10, greater than 8 to about 10, greater than 7, greater than 7.5, greater than 8, greater than 9, or from about 8.5 to about 10.

Zinc Ion Source

The oral care composition can comprise zinc, such as from a zinc ion source. The zinc ion source can comprise one or more zinc containing compounds, such as zinc fluoride, zinc lactate, zinc oxide, zinc phosphate, zinc chloride, zinc acetate, zinc hexafluorozirconate, zinc sulfate, zinc tartrate, zinc gluconate, zinc citrate, zinc malate, zinc glycinate, zinc pyrophosphate, zinc metaphosphate, zinc oxalate, and/or zinc carbonate. The zinc ion source can be a fluoride-free zinc ion source, such as zinc phosphate, zinc oxide, and/or zinc citrate.

The zinc ion source may be present in the total oral care composition at an amount of from about 0.01% to about 10%, from about 0.2% to about 1%, from about 0.5% to about 1.5%, or from about 0.3% to about 0.6%, by weight of the dentifrice composition.

Polyphosphates

The oral care composition can comprise polyphosphate, such as from a polyphosphate source. A polyphosphate source can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. Alkali earth metal cations, such as calcium, are not preferred because they tend to form insoluble fluoride salts from aqueous solutions comprising a fluoride ions and alkali earth metal cations. Thus, the oral care compositions disclosed herein can be free of, essentially free of, or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Ascaris.

The oral care composition can comprise from about 0.01% to about 15%, from about 0.11% to about 10%, from about 0.5% to about 5%, from about 1 to about 20%, or about 10% or less, by weight of the oral care composition, of the polyphosphate source.

Humectants

The oral care composition can comprise one or more humectants, have low levels of a humectant, be essentially free of, substantially free of, or be free of a humectant. Humectants serve to add body or "mouth texture" to an oral care composition or dentifrice as well as preventing the dentifrice from drying out. Suitable humectants include polyethylene glycol (at a variety of different molecular weights), propylene glycol, glycerin (glycerol), erythritol, xylitol, sorbitol, mannitol, butylene glycol, lactitol, hydrogenated starch hydrolysates, and/or mixtures thereof. The oral care composition can comprise one or more humectants each at a level of from 0 to about 70%, from about 5% to about 50%, from about 10% to about 60%, or from about 20% to about 80%, by weight of the oral care composition.

Surfactants

The oral care composition can comprise one or more surfactants. The surfactants can be used to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants.

Suitable anionic surfactants include, for example, the water soluble salts of alkyl sulfates having from 8 to 20 carbon atoms in the alkyl radical and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants include sarcosinates, such as sodium lauroyl sarcosinate, taurates, sodium lauryl sulfoacetate, sodium lauroyl isethionate, sodium laureth carboxylate, and sodium dodecyl benzene sulfonate. Combinations of anionic surfactants can also be employed.

Another suitable class of anionic surfactants are alkyl phosphates. The surface active organophosphate agents can have a strong affinity for enamel surface and have sufficient surface binding propensity to desorb pellicle proteins and remain affixed to enamel surfaces. Suitable examples of organophosphate compounds include mono-, di- or triesters represented by the general structure below wherein $Z_1$, $Z_2$, or $Z_3$ may be identical or different with at least one being an organic moiety. $Z_1$, $Z_2$, or $Z_3$ can be selected from linear or branched, alkyl or alkenyl group of from 1 to 22 carbon atoms, optionally substituted by one or more phosphate groups; alkoxylated alkyl or alkenyl, (poly)saccharide, polyol or polyether group.

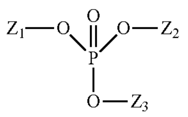

Some other agents include alkyl or alkenyl phosphate esters represented by the following structure:

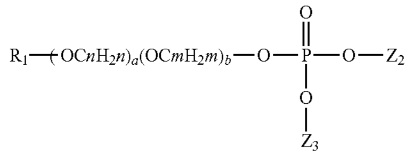

wherein $R_1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z and Z may be identical or different, each represents hydrogen, alkali metal, ammonium, protonated alkyl amine or protonated functional alkylamine, such as analkanolamine, or a R—(OCH2)(OCH)— group. Examples of suitable agents include alkyl and alkyl (poly) alkoxy phosphates such as lauryl phosphate; PPGS ceteareth-10 phosphate; laureth-1 phosphate; laureth-3 phosphate; laureth-9 phosphate; trilaureth-4 phosphate; $C_{12-18}$ PEG 9 phosphate: and sodium dilaureth-10 phosphate. The alkyl phosphate can be polymeric. Examples of polymeric alkyl phosphates include those containing repeating alkoxy groups as the polymeric portion, in particular 3 or more ethoxy, propoxy isopropoxy or butoxy groups.

Other suitable anionic surfactants are sarcosinates, isethionates and taurates, especially their alkali metal or ammonium salts. Examples include: lauroyl sarcosinate, myristoyl sarcosinate, palmitoyl sarcosinate, stearoyl sarcosinate oleoyl sarcosinate, or combinations thereof.

Other suitable anionic surfactants include sodium or potassium alkyl sulfates, such as sodium lauryl sulfate, acyl isethionates, acyl methyl isethionates, alkyl ether carboxylates, acyl alaninates, acyl gulatames, acyl glycinates, acyl sarconsinates, sodium methyl acyl taurates, sodium laureth sulfosuccinates, alpha olefin sulfonates, alkyl benze sulfonates, sodium lauroyl lactylate, sodium laurylglucosides hydroxypropyl sulfonate, and/or combinations.

Zwitterionic or amphoteric surfactants useful herein include derivatives of aliphatic quaternary ammonium, phosphonium, and Sulfonium compounds, in which the aliphatic radicals can be straight chain or branched, and one of the aliphatic substituents contains from 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577. Typical alkyl dimethyl betaines include decyl betaine or 2-(N-decyl-N,N-dimethylammonio) acetate, coco-betaine or 2-(N-coco-N,N-dimethyl ammonio)acetate, myristyl betaine, palmityl betaine, lauryl betaine, cetyl betaine, cetyl betaine, stearyl betaine, etc. The amidobetaines can be exemplified by cocoamidoethyl betaine, cocoamidopropyl betaine (CADB), and lauramidopropyl betaine. Other suitable amphoteric surfactants include betaines, sultaines, sodium laurylamphoacetates, alkylamphodiacetates, and/or combinations thereof.

Cationic surfactants useful in the present invention include, for example, derivatives of quaternary ammonium compounds having one long alkyl chain containing from 8 to 18 carbon atoms such as lauryl trimethylammonium chloride; cetyl pyridinium chloride; cetyl trimethyl-ammonium bromide; cetyl pyridinium fluoride or combinations thereof.

Nonionic surfactants that can be used in the compositions of the present invention include, for example, compounds produced by the condensation of alkylene oxide groups (hydrophilic in nature) with an organic hydrophobic compound which may be aliphatic or alkylaromatic in nature. Examples of suitable nonionic surfactants can include the Pluronics® which are poloxamers, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and combinations of such materials. Other suitable non-ionic surfactants includes alkyl glucamides, alkyl glucosides, and/or combinations thereof.

The one or more surfactants can also include one or more natural and/or naturally derived surfactants. Natural surfactants can include surfactants that are derived from natural products and/or surfactants that are minimally or not processed. Natural surfactants can include hydrogenated, non-hydrogenated, or partially hydrogenated vegetable oils, olus oil, *Passiflora incarnata* oil, candelilla cera, coco-caprylate, caprate, dicaprylyl ether, lauryl alcohol, myristyl myristate, dicaprylyl ether, caprylic acid, caprylic ester, octyl decanoate, octyl octanoate, undecane, tridecane, decyl oleate, oleic acid decylester, cetyl palmitate, stearic acid, palmitic acid, glyceryl stearate, hydrogenated, non-hydrogenated, or partially hydrogenated vegetable glycerides, Polyglyceryl-2 dipolyhydroxystearate, cetearyl alcohol, sucrose polystearate, glycerin, octadodecanol, hydrolyzed, partially hydrolyzed, or non-hydrolyzed vegetable protein, hydrolyzed, partially hydrolyzed, or non-hydrolyzed wheat protein hydrolysate, polyglyceryl-3 diisostearate, glyceryl oleate, myristyl alcohol, cetyl alcohol, sodium cetearyl sulfate, cetearyl alcohol, glyceryl laurate, capric triglyceride, coco-glycerides, lectithin, dicaprylyl ether, xanthan gum, sodium coco-sulfate, ammonium lauryl sulfate, sodium cocoyl sulfate, sodium cocoyl glutamate, polyalkylglucosides, such as decyl glucoside, cetearyl glucoside, cetyl stearyl polyglucoside, coco-glucoside, and lauryl glucoside, and/or combinations thereof. Natural surfactants can include any of the Natrue ingredients marketed by BASF, such as, for example, CegeSoft®, Cetiol®, Cutina®, Dehymuls®, Emulgade®, Emulgin®, Eutanol®, Gluadin®, Lameform®, LameSoft®, Lanette®, Monomuls®, Myritol®, Plantacare®, Plantaquat®, Platasil®, Rheocare®, Sulfopon®, Texapon®, and/or combinations thereof.

Other specific examples of surfactants include sodium lauryl sulfate, sodium lauryl isethionate, sodium lauroyl methyl isethionate, sodium cocoyl glutamate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine, sodium cocoyl glutamate, and the like. Additional surfactants desired include fatty acid salts of glutamate, alkyl glucoside, salts of taurates, betaines, caprylates, and/or mixtures thereof. The oral care composition can also be sulfate free.

The oral care composition can comprise one or more surfactants each at a level from about 0.01% to about 15%, from about 0.3% to about 10%, or from about 0.3% to about 2.5%, by weight of the oral care composition.

Thickening Agents

The oral care composition can comprise one or more thickening agents. Thickening agents can be useful in the oral care compositions to provide a gelatinous structure that stabilizes the dentifrice and/or toothpaste against phase separation. Suitable thickening agents include polysaccharides, polymers, and/or silica thickeners.

The thickening agent can comprise one or more polysaccharides. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, microcrystalline cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

Other polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise one or more polymers. The polymer can be a polyethylene glycol (PEG), a polyvinylpyrrolidone (PVP), polyacrylic acid, a polymer derived from at least one acrylic acid monomer, a copolymer of maleic anhydride and methyl vinyl ether, a crosslinked polyacrylic acid polymer, of various weight percentages of the oral care composition as well as various ranges of average molecular ranges. Alternatively, the oral care composition can be free of, essentially free of, or substantially free of a copolymer of maleic anhydride and methyl vinyl ether.

The thickening agent can comprise one or more inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

The oral care composition can comprise from 0.01% to about 15%, from 0.1% to about 10%, from about 0.2% to about 5%, or from about 0.5% to about 2% of one or more thickening agents.

Prenylated Flavonoids

The oral care composition of the present invention can comprise prenylated flavonoid. Flavonoids are a group of natural substances found in a wide range of fruits, vegetables, grains, bark, roots, stems, flowers, tea, and wine. Flavonoids can have a variety of beneficial effects on health, such as antioxidative, anti-inflammatory, antimutagenic, anticarcinogenic, and antibacterial benefits. Prenylated flavonoids are flavonoids that include at least one prenyl functional group (3-methylbut-2-en-1-yl, as shown in Formula VIII), which has been previously identified to facilitate attachment to cell membranes. Thus, while not wishing to being bound by theory, it is believed that the addition of a prenyl group, i.e. prenylation, to a flavonoid can increase the activity of the original flavonoid by increasing the lipophilicity of the parent molecule and improving the penetration of the prenylated molecule into the bacterial cell membrane. Increasing the lipophilicity to increase penetration into the cell membrane can be a double-edged sword because the prenylated flavonoid will tend towards insolubility at high Log P values (high lipophilicity). Log P can be an important indicator of antibacterial efficacy.

As such, the term prenylated flavonoids can include flavonoids found naturally with one or more prenyl functional groups, flavonoids with a synthetically added prenyl functional group, and/or prenylated flavonoids with additional prenyl functional groups synthetically added.

Formula VIII

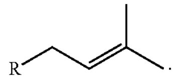

Prenyl Function Group with R representing the other portions of the molecule

Other suitable functionalities of the parent molecule that improve the structure-activity relationship (e.g., structure-MIC relationship) of the prenylated molecule include additional heterocycles containing nitrogen or oxygen, alkylamino chains, or alkyl chains substituted onto one or more of the aromatic rings of the parent flavonoid.

Flavonoids can have a 15-carbon skeleton with at least two phenyl rings and at least one heterocyclic ring. Some suitable flavonoid backbones can be shown in Formula IX (flavone backbone), Formula X (isoflavan backbone), and/or Formula XI (neoflavonoid backbone).

Formula IX

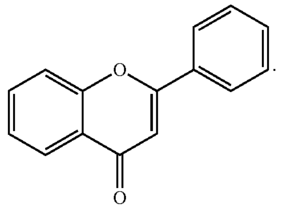

Flavone Backbone

Formula X

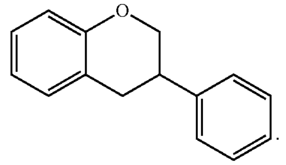

Isoflavan backbone

Formula XI

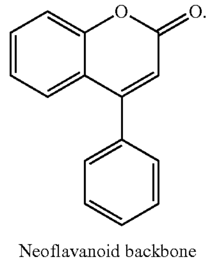

Neoflavanoid backbone

Other suitable subgroups of flavonoids include anthocyanidins, anthoxanthins, flavanones, flavanonols, flavans, isoflavonoids, chalcones and/or combinations thereof.

Prenylated flavonoids can include naturally isolated prenylated flavonoids or naturally isolated flavonoids that are synthetically altered to add one or more prenyl functional groups through a variety of synthetic processes that would be known to a person of ordinary skill in the art of synthetic organic chemistry.

Other suitable prenylated flavonoids can include Bavachalcone, Bavachin, Bavachinin, Corylifol A, Epimedin A, Epimedin A1, Epimedin B, Epimedin C, Icariin, Icariside I, Icariside II, Icaritin, Isobavachalcone, Isoxanthohumol, Neobavaisoflavone, 6-Prenylnaringenin, 8-Prenylnaringenin, Sophoraflavanone G, (−)-Sophoranone, Xanthohumol, Quercetin, Macelignan, Kuraridin, Kurarinone, Kuwanon G, Kuwanon C, Panduratin A, 6-geranylnaringenin, Australone A, 6,8-Diprenyleriodictyol, dorsmanin C, dorsmanin F, 8-Prenylkaempferol, 7-O-Methylluteone, luteone, 6-prenylgenistein, isowighteone, lupiwighteone, and/or combinations thereof. Other suitable prenylated flavonoids include cannflavins, such as Cannflavin A, Cannflavin B, and/or Cannflavin C.

Preferably, the prenylated flavonoid has a high probability of having an MIC of less than about 25 ppm for *S. aureus*, a gram-positive bacterium. Suitable prenylated flavonoids include Bavachin, Bavachinin, Corylifol A, Icaritin, Isoxanthohumol, Neobavaisoflavone, 6-Prenylnaringenin, 8-Prenylnaringenin, Sophoraflavanone G, (−)-Sophoranone, Kurarinone, Kuwanon C, Panduratin A, and/or combinations thereof.

Preferably, the prenylated flavonoid has a high probability of having an MIC of less than about about 25 ppm for *E. coli*, a gram-negative bacterium. Suitable prenylated flavonoids include Bavachinin, Isoxanthohumol, 8-Prenylnaringenin, Sophoraflavanone G, Kurarinone, Panduratin A, and/or combinations thereof.

Approximately 1000 prenylated flavonoids have been identified from plants. According to the number of prenylated flavonoids reported before, prenylated flavonones are the most common subclass and prenylated flavanols is the rarest sub-class. Even though natural prenylated flavonoids have been detected to have diversely structural characteristics, they have a narrow distribution in plants, which are different to the parent flavonoids as they are present almost in all plants. Most of prenylated flavonoids are found in the following families, including *Cannabaceae, Guttiferae, Leguminosae, Moraceae, Rutaceae* and *Umbelliferae. Leguminosae* and *Moraceae*, due to their consumption as fruits and vegetables, are the most frequently investigated families and many novel prenylated flavonoids have been explored. *Humulus lupulus* of the *Cannabaceae* include 8-prenylnaringenin and xanthohumol, which play an important role in the health benefits of beer.

The prenylated flavonoid can be incorporated through a hops extract, incorporated in a separately added extract, or added as a separate component of the oral care compositions disclosed herein.

Other Ingredients

The oral care composition can comprise a variety of other ingredients, such as flavoring agents, sweeteners, colorants, preservatives, buffering agents, or other ingredients suitable for use in oral care compositions, as described below.

Flavoring agents also can be added to the oral care composition. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") or N-(Ethoxycarbonylmethyl)-3-p-menthanecarboxamide (known commercially as "WS-5"), and mixtures thereof. A flavor system is generally used in the compositions at levels of from about 0.001% to about 5%, by weight of the oral care composition. These flavoring agents generally comprise mixtures of aldehydes, ketones, esters, phenols, acids, and aliphatic, aromatic and other alcohols.

Sweeteners can be added to the oral care composition to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, sucralose, stevia, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Preservatives also can be added to the oral care compositions to prevent bacterial growth. Suitable preservatives approved for use in oral compositions such as methylparaben, propylparaben, benzoic acid, and sodium benzoate can be added in safe and effective amounts.

Titanium dioxide may also be added to the present composition. Titanium dioxide is a white powder which adds opacity to the compositions. Titanium dioxide generally comprises from about 0.25% to about 5%, by weight of the oral care composition.

Other ingredients can be used in the oral care composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

TABLE 1

| Compositions | | | | |
|---|---|---|---|---|
| | Amount (Wt %) | | | |
| Ingredients | Ex 1 | Ex. 2 | Ex. 3 | Ex. 4 |
| Sorbitol | — | 34.67 | 34.67 | 34.67 |
| Water | — | 13.00 | 11.00 | 9.00 |
| Sodium Carboxymethyl Cellulose | — | 1.00 | 1.00 | 1.00 |
| Xanthan Gum | — | 0.30 | 0.30 | 0.30 |
| Stannous Chloride silica blend | — | 1.10 | 1.10 | 1.10 |
| Sodium Gluconate | — | 1.00 | 1.00 | 1.00 |
| Sodium Bicarbonate | — | 10.00 | 10.00 | 10.00 |
| Glycine | — | — | 2.00 | 4.00 |
| Calcium Carbonate | — | 32.00 | 32.00 | 32.00 |
| Hops | — | 0.50 | 0.50 | 0.50 |
| Sodium Lauryl Sulfate (28% soln.) | — | 4.60 | 4.60 | 4.60 |

TABLE 1-continued

| Compositions | | | | |
|---|---|---|---|---|
| | Amount (Wt %) | | | |
| Ingredients | Ex 1 | Ex. 2 | Ex. 3 | Ex. 4 |
| Sodium Hydroxide (50%) | — | 0.33 | 0.33 | 0.33 |
| Sucralose | — | 0.20 | 0.20 | 0.20 |
| Sodium Saccharin | — | 0.50 | 0.50 | 0.50 |
| Flavor/sensate oils | — | 0.80 | 0.80 | 0.80 |
| NaCl | 0.800 | | | |
| KCL | 0.020 | | | |
| $Na_2HPO_4$ | 0.142 | | | |
| $KH_2PO_4$ | 0.024 | | | |
| Water | 99.014 | | | |
| Total | 100% | 100% | 100% | 100% |

Assay for Measuring Biofilm Architecture, Penetration of Anti-Bacterial Agent & Endotoxin Neutralization in the Biofilms The following assay was used an in situ plaque biofilm for inventive oral care compositions of the present invention in order to determine:

1—the biofilm EPS matrix destablisation and thickness of the dental biofilm by measuring fluorescent light emitted from the labeled EPS biofilm;

2—penetration efficiency of stannous ions with bacteria via measurement of co-localization percentage 3—improved endotoxin neutralization of anti-bacterial agent in the biofilms via LPS binding efficiency of stannous ions via measurement of a fluorescent dye that is bound to lipid A of LPS Details of the assay are described below.

(a) Substrate for Biofilm Growth

Hydroxyapatite ("HA") disks were used for in situ growth of biofilms. The HA disks are designed having three parallel grooves (i.e., 200 μm wide; 200 μm deep for two sides' grooves; while 500 μm wide and 500 μm deep for the middle groove) in each disk. When attaching disks to subject's mouth, keep these grooves vertical, to mimic interproximal gap between teeth, which is the hard-to-clean area where plaque generally tends to accumulate. This model allows the collection of undisturbed plaque from the grooves. HA disks are manufactured by Shanghai Bei'erkang biomedicine limited company (Shanghai, China).

(b) Wearing the Splint

Figure 2:
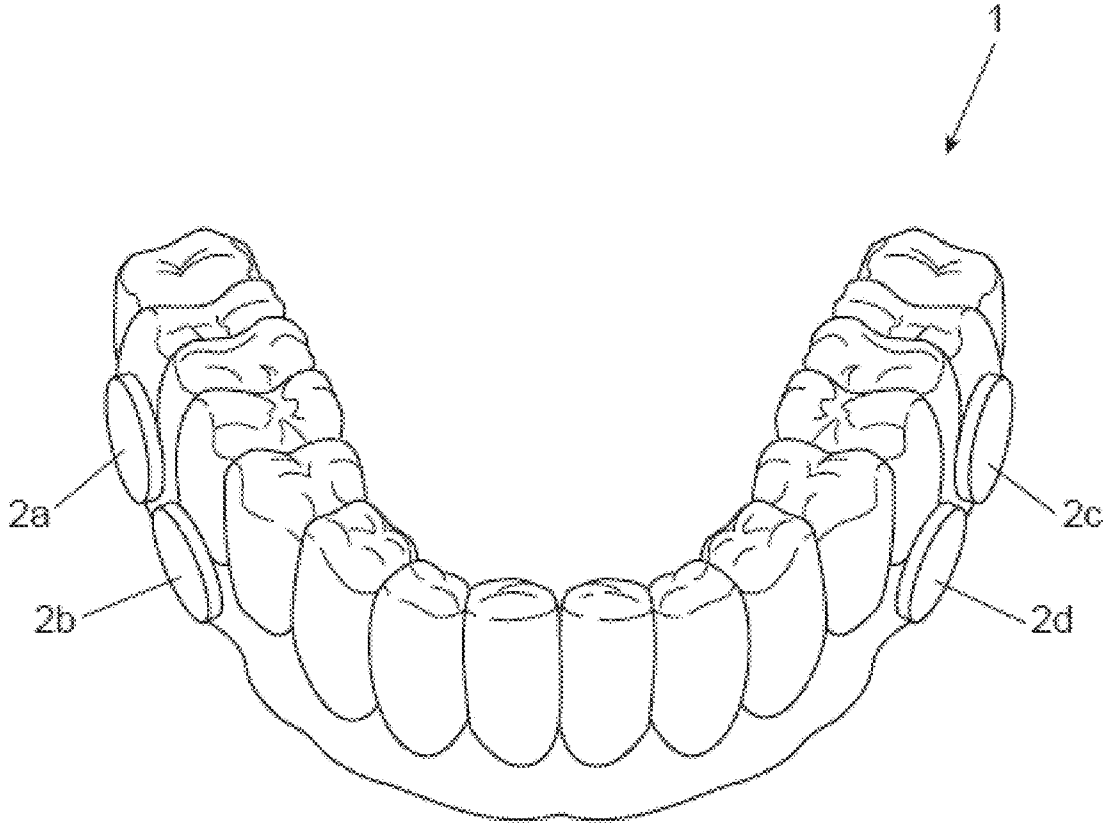
FIG. 2 shows an oral splint with hydroxyapatite disks.
Figure 3:
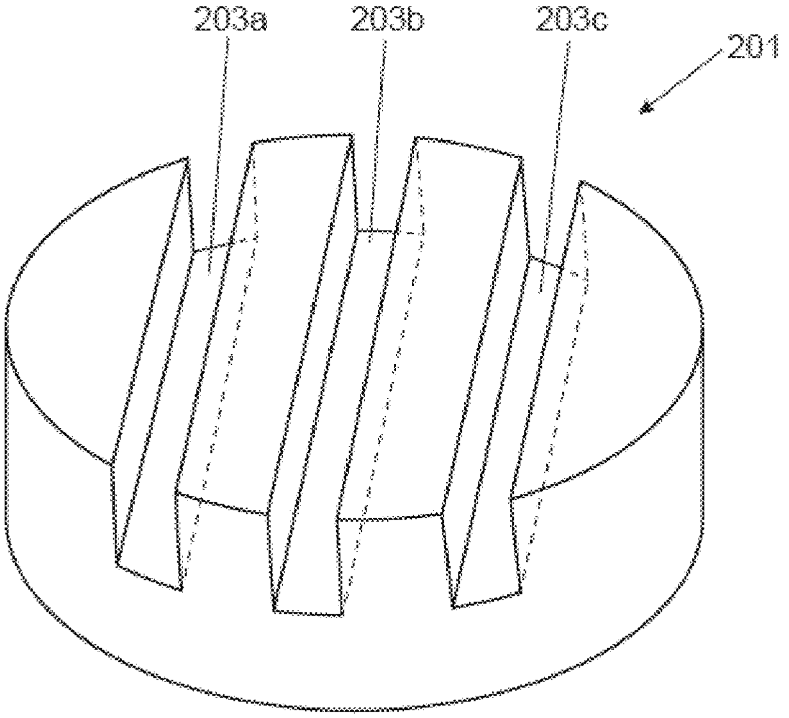
FIG. 3 shows a hydroxyapatite disk having grooves.
Figure 4:
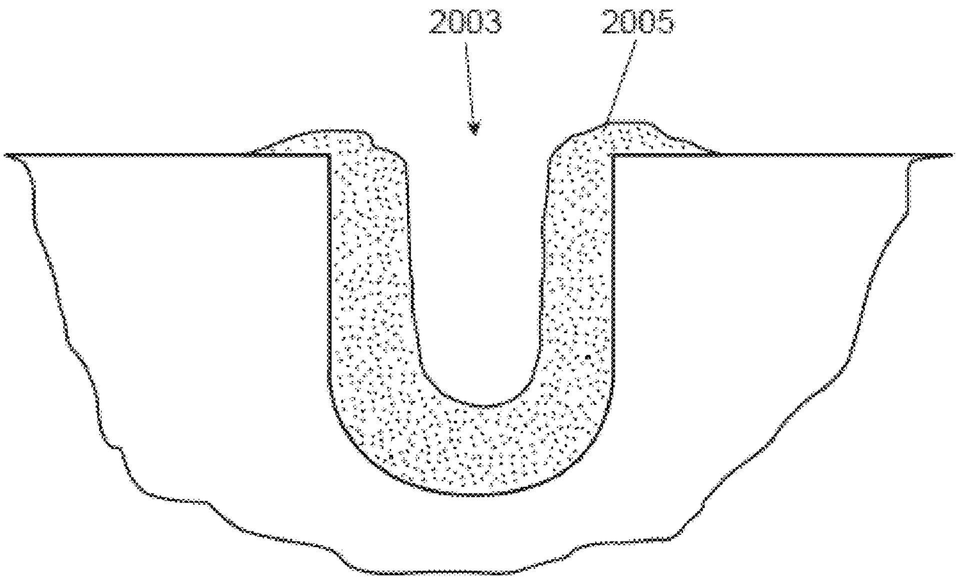
FIG. 4 shows a cross-sectional view of the grooves.

Human subjects wore the splint. Each subject wore up to 12 HA disks on the splint to ensure that, at least, 9 HA disks were available after 48 hours. A non-limiting example of such a splint and HA disks are shown in FIG. 2. With reference to FIG. 2, the device (1) holds a plurality of HA disks (2*a*-2*d*). In a specific example, and with reference to FIG. 3, the HA disk (201) has three parallel grooves (203) (the two sides' grooves (203*a* and 203*c*) are 300 μm wide and 300 μm deep; while the middle grove (203*b*) (in between the two side grooves) is 500 μm wide and 500 μm deep). The middle groove is designed wider and deeper than the two sides' grooves so that the HA disk can be more easily separated into two identical half-disks for head-to-head comparison purposes. FIG. 4 is a schematic of a cross-sectional view of the groove (2003) with biofilm (2005) therein. Further details of the HA disks are described in US2017/0056531 (e.g. paragraphs [0019]-[0020]).

Although not shown in FIG. 4, the disks can be positioned such that the recede is in the inter-dental space between the teeth (since this location is prone to plaque (given the difficulty in cleaning, etc.)). The subjects withdrew the splint only during meals (the splint stored in an opaque container in humid conditions) and to perform oral hygiene procedures Immediately thereafter, the splint was worn again. Subjects were asked to use a straw when drinking.

(c) In-situ Biofilms Release from HA Desk

All HA disks were removed from the splint at 48 hours by tweezers. Tweezers were used to hold the edge of HA chips and transfer the HA disk to a 2 mL centrifuge tube containing PBS (phosphate buffered saline) solution. Tweezers were washed thoroughly (water; 75% alcohol; and then deionized water) before every disk transfer.

(d) Preparation of Toothpaste Supernatant 15 grams of deionized water is added to 5 grams toothpaste (using any one of the Examples 1-5). After stirring thoroughly, the mixture is centrifuge at 12,000 RPM for 20 minutes. The supernatant is prepared one day before usage and stored at 4° C.

(e) Confocal Laser Scanning Microscopy

After the HA disks were removed from the splint. The HA disks were used for ex vivo treatment by the different inventive and comparative compositions. After being treated with the subject supernatant and labeled with microbial fluorescent probe and stannous fluorescent probe (such as described in US2018/0072944A1; Shi et al.), the biofilms in the grooves were measured by confocal laser scanning microscopy ("CLSM") (as described below).

(f) Disk Preparation

The HA disks were rinsed in PBS solution and each HA disk was divided into two halves by tweezers. Thereafter, each half-disk was placed into 500-1000 μL of PBS solution statically for 1 minute. Each disk was treated for two minutes by either PBS solution or toothpaste supernatant. Each disk was washed by holding each disk with tweezers, shaken for ten rounds of back and forth in 1 mL of PBS solution, and then this washing cycle was repeated. Then each disk was immersed into 500-1000 μL PBS solution statically for 5 minutes.

After being treated with PBS and/or the oral care composition (e.g., toothpaste) supernatant and labeled with specific fluorescent probes, the biofilm in the grooves was measured by confocal laser scanning microscopy (CLSM).

(g) Fluorescence Probe Staining and Microscopy

"Ion fluorescent probe" means a fluorescent probe that specifically binds to one kind of ions and emit fluorescence at a certain wavelength. In recent years, significant emphasis has been placed on the development of new, highly selective fluorescent probes of ions because of their potential applications in biochemistry and environmental research. Many kinds of signaling mechanisms have been proposed and utilized for optical detection of ions, including photo-induced electron/energy transfer (PET), intramolecular charge transfer (ICT), fluorescence resonance energy transfer (FRET), and so on. Some of these fluorescent probes can also be applied in fluorescence bioimaging, which causes little cell damage and is highly sensitive with high-speed spatial analysis of living cells. Specifically, FRET imaging that affords simultaneous recording of two emission intensities at different wavelengths in the presence and absence of analytes has provided a facile method for visualizing complex biological processes at the molecular level. This technique appears to be suited to the study of physiological functions or pathogenesis of ions in biofilm and human body.

Stannous penetration efficiency of stannous ions with bacteria was measured via co-localization percentage. Non-limiting examples of a stannous fluorescent probe suitable for labeling the biofilm may include any one following of the compounds: (a) tert-butyl (3',6'-diamino-3-oxospiro[isoindoline-1,9'-xanthen]-2-yl)carbamate; (b) tert-butyl (3',6'-bis(dimethylamino)-3-oxospiro[isoindoline-1,9'-xanthen]-2-yl)carbamate; (c) tert-butyl (3',6'-bis(diethylamino)-3-oxospiro[isoindoline-1,9'-xanthen]-2-yl)carbamate; (d) tert-butyl (3',6'-bis(ethylamino)-2',7'-dimethyl-3-oxospiro[isoindoline-1,9'-xanthen]-2-yl)carbamate; (e) tert-butyl (3',6'-diamino-2',7'-dimethyl-3-oxospiro[isoindoline-1,9'-xanthen]-2-yl)carbamate; (f) tert-butyl (3-oxo-3',6'-di(pyrrolidin-1-yl)spiro[isoindoline-1,9'-xanthen]-2-yl)carbamate; (g) tert-butyl (3-oxo-3',6'-bis(phenylamino)spiro[isoindoline-1,9'-xanthen]-2-yl)carbamate; (h) tert-butyl (3-oxo-3',6'-di(piperidin-1-yl)spiro[isoindoline-1,9'-xanthen]-2-yl)carbamate; (i) tert-butyl (3',6'-dimorpholino-3-oxospiro[isoindoline-1,9'-xanthen]-2-yl)carbamate; (j) tert-butyl (2',7'-dibutyl-3',6'-bis(diethylamino)-3-oxospiro[isoindoline-1,9'-xanthen]-2-yl)carbamate; (k) tert-butyl (2',7'-dimethyl-3-oxo-3',6'-di(piperidin-1-yl)spiro[isoindoline-1,9'-xanthen]-2-yl)carbamate; (l) tert-butyl (3-oxo-1',2',3',4',10',11',12',13'-octahydrospiro[isoindoline-1,7'-pyrano[2,3-f:6,5-f']diquinolin]-2-yl)carbamate; (m) tert-butyl (3-oxo-1',2',3',4',8',9',10',11'-octahydrospiro[isoindoline-1,6'-pyrano[3,2-g:5,6-g']diquinolin]-2-yl)carbamate; (n) N-(3',6'-bis(diethylamino)-3-oxospiro[isoindoline-1,9'-xanthen]-2-yl)propionamide; (p) N-(3',6'-bis(diethylamino)-3-oxospiro[isoindoline-1,9'-xanthen]-2-yl)butyramide; and (q) N-(3',6'-bis(diethylamino)-3-oxospiro[isoindoline-1,9'-xanthen]-2-yl)pentanamide. Preferably the stannous probe is selected from: N-(3',6'-bis(diethylamino)-3-oxospiro[isoindoline-1,9'-xanthen]-2-yl)propionamide; N-(3',6'-bis(diethylamino)-3-oxospiro[isoindoline-1,9'-xanthen]-2-yl)butyramide; and N-(3',6'-bis(diethylamino)-3-oxospiro[isoindoline-1,9'-xanthen]-2-yl)pentanamide.

Generally these stannous fluorescent probes contain a Rhodamine B derivative moiety as fluorophore, linked via amide moiety to a carbazate group. Further details are described in the WO 2015/139577 A1 (24 Sep. 2015) or US equivalent publication thereof. Preferably, the stannous fluorescent probe is tert-butoxy-carboxamide,N-[3',6'-bis(diethylamino)-3-oxospiro[1H-isoindole-1,9'-[9H]xanthen]-H)-yl]

The "Microbial fluorescent probe" means a fluorescent probe that binds to microbes of a biofilm and emit fluorescence at a certain wavelength. One class of such probes includes fluorescently labeled oligonucleotides, preferably rRNA-directed oligonucleotides. Non-limiting examples include SYTO™ branded dyes. One specific example is SYTO® 9 Green Fluorescent Nucleic Acid Stain, wherein excitation is a 485 (DNA) and 486 (RNA), and light emission is detected at 498 (DNA) and 501 (RNA).

After treatment and immersing, each half-disk was stained with the Sn probe together with Syto-9 probe (containing 5 μM Syto-9 and 5 μM Sn probe) for 30 minutes in the dark. The SYTO-9/Sn dye stained samples, the following parameters were used: λex=488 nm/560 nm, λem=500/580 nm, 20× objective lens, and scanning from bottom of surface bacteria for 60 μm with step size=3 μm.

The LPS neutralization effect was evaluated using BODIPY-TR-cadaverine (BC), a fluorescent dye that is bound to lipid A, thereby suppressing its fluorescence. BC is displaced by agents with an affinity for this lipid. When LPS are bound by other ions, e.g., stannous, BC is released from the LPS and its fluorescence is proportional to the amount of free (unbound) BC present. Therefore, the level of fluorescence indicates the amount of neutralized (bound) LPS versus free (unbound) LPS, and the efficacy of an antibacterial agent in reducing the biofilm's toxicity. The greater the amount of bound LPS, the lower its toxicity.

After treatment and immersing, each half-disk was stained with the BODIPY-TR-cadaverine (BC) probe together with Syto-9 probe (containing 5 μM Syto-9 and 5 μM BC probe) for 30 minutes in the dark. After staining, each disk was immersed into 500-1000 μL PBS solution statically for 2 minutes. The disks were washed again, by holding each disk with tweezers, shaken for five rounds of back and forth in 1 mL PBS solution, and repeated. For SYTO-9/BC dye stained samples, the following parameters were used: λex=488 nm/589 nm, λem=500/616 nm, 20× objective lens, and scanning from bottom of surface bacteria for 60 μm with step size=3 μm.

Fluorescence labeled calcium probes are molecules that exhibit an increase in fluorescence upon binding $Ca^{2+}$. The biofilm was labeled with a calcium fluorescent probe. Examples of a calcium fluorescent probe suitable for labeling the biofilm may be any one or more of the following compounds:

(a) Fluo-3™, AM™, cell permeant fluorescence stains;
(b) Fluo-3™, Pentapotassium Salt, cell impermeant fluorescence stains;
(c) Fluo-4™, AM™, cell permeant fluorescence stains;
(d) Fluo-4™, Pentapotassium Salt, cell impermeant fluorescence stains;
(e) Fluo-4 Direct™ Calcium Assay Kit;
(f) Mag-Fluo-4™, Tetrapotassium Salt, cell impermeant fluorescence stains; and
(g) Fluo-5F™, AM™, cell permeant fluorescence stains.

One or more of these probes may be available from ThermoFisher Scientific Company, Waltham, MA.

Fluo-3™ was used to image the spatial dynamics of $Ca^{2+}$ signaling. Biofilm may be treated with the AM™ ester forms of calcium probes by adding the dissolved probe directly to biofilm. Fluo-3™, AM™, cell permeant fluorescent probes are used for intracellular and extracellular calcium staining using confocal microscopy, flow cytometry, and microplate screening applications (absorption/emission maxima~506/526 nm). It is reported that the Concanavalin A™ (Con A), Alexa Fluor® 594 Conjugate is a reliable alternative to stain EPS of biofilm. Alexa Fluor® 594 conjugate of Con A exhibits the bright, red fluorescence of the Alexa Fluor® 594 dye (absorption/emission maxima ~590/617 nm). Concanavalin A™, Alexa Fluor® 594 Conjugate selectively bound to α-mannopyranosyl and α-glucopyranosyl residues which are rich in EPS part of biofilm.

One specific example is Concanavalin A™, Fluorescein Conjugate™, wherein excitation is 494 nm, and maximum light emission is detected at 518 nm. These EPS fluorescent probes are widely available as well as the procedure details in how to use them to quantitatively determine the location and/or amount of EPS.

Examples of an EPS fluorescent probe suitable for labeling the biofilm may be any one of the following compounds:

(a) Molecular Probes™ Concanavalin A™ Alexa Fluor® 350 Conjugate™;
(b) Molecular Probes™ Concanavalin A™ Alexa Fluor® 488 Conjugate™;
(c) Molecular Probes™ Concanavalin A™ Alexa Fluor® 594 Conjugate™;
(d) Molecular Probes™ Concanavalin A™ Alexa Fluor® 633 Conjugate™;
(e) Molecular Probes™ Concanavalin A™ Alexa Fluor® 647 Conjugate™;

(f) Molecular Probes™ Concanavalin A™ Fluorescein Conjugate™;

(g) Molecular Probes™ Concanavalin A™ Oregon Green® 488 Conjugate™;

(h) Molecular Probes™ Concanavalin A™ tetramethyl-rhodamine Conjugate™; and (i) Molecular Probes™ Concanavalin A™ Texas Red® Conjugate™.

One or more of these probes may be available from ThermoFisher Scientific Company, Waltham, MA.

After treatment and immersing, each half-disk specimen was stained with a dye mixture solution of the Fluo-3™, AM™, cell permeant fluorescent probe together with Concanavalin A™, Alexa Fluor® 594 Conjugate probe (containing 5 uM Fluo-3™+5 uM Con-A™) for 30 minutes in the dark. After staining, each specimen was immersed into 500-1000 ul PBS solution statically for 2 minutes. The disks were washed again, by holding each disk with tweezers, shaken for five rounds of back and forth in 1 mL PBS solution, and repeated. For Fluo-3™, AM™/Fluor® 594 Conjugate dye stained samples, the following parameters were used: λex=506 nm/590 nm, λem=526/617 nm, 20× objective lens, and scanning from bottom of surface bacteria for 60 μm with step size=3 μm.

(h) Confocal Laser Scanning Microscopy

The Leica™ TCS SP8 AOBS spectral confocal microscope was used. The confocal system consists of a Leica™ DM6000B upright microscope and a Leica™ DMIRE2 inverted microscope. An upright stand was used for applications involving slide-mounted specimens; whereas the inverted stand, having a 37° C. incubation chamber and $CO_2$ enrichment accessories, provided for live cell applications. The microscopes shared an exchangeable laser scan head and, in addition to their own electromotor-driven stages, a galvanometer-driven high precision Z-stage which facilitates rapid imaging in the focal (Z) plane. In addition to epifluorescence, the microscopes supported a variety of transmitted light contrast methods including bright field, polarizing light and differential interference contrast, and are equipped with 5×, 20×, 40×, 63×(oil and dry) and 100× (oil) Leica™ objective lenses.

The laser scanning and detection system is described. The TCS SP8 AOBS confocal system was supplied with four lasers (one diode, one argon, and two helium neon lasers) thus allowing excitation of a broad range of fluorochromes within the UV, visible and far red ranges of the electromagnetic spectrum. The design of the laser scan head, which incorporated acousto-optical tunable filters (“AOTF”), an acousto-optical beam splitter (“AOBS”) and four prism spectrophotometer detectors, permitted simultaneous excitation and detection of three fluorochromes. The upright microscope also had a transmission light detector making it possible to overlay a transmitted light image upon a fluorescence recording.

Leica™ Confocal software LAS AF3.3.0 was used. The confocal was controlled via a standard Pentium PC equipped with dual monitors and running Leica™ Confocal Software. The Leica Confocal Software LAS AF3.3.0 (available from Leica Lasertechnik GmbH, Heidelberg, Germany) provided an interface for multi-dimensional image series acquisition, processing and analysis, that included 3D reconstruction and measurement, physiological recording and analysis, time-lapse, fluorochrome co-localization, photo-bleaching techniques such as FRAP and FRET, spectral immixing, and multicolour restoration.

(i) Image Analysis

Sn Analysis; The SYTO-9/Sn dye stained samples were chosen to quantify overlap efficiency of red and green pixels. Using the software, the pixel overlap of “green” bacterial probes and that of “red” stannous probes were identified, and then this value is divided by all non-black pixels (that include non-overlapping stannous probes) to provide a co-localization percentage of stannous in bacteria. Generally, the higher this co-localization percentage, the more efficacious the oral care product was in delivering stannous into bacteria. (See Xiang J, Li H, Pan B, Chang J, He Y, He T, Strand R, Shi Y, Dong W. (2018) Penetration and Bactericidal Efficacy of Two Oral Care Products in an Oral Biofilm Model. *Am J Dent, Vol.* 31, Issue 1: 53-60)

LPS Analysis; The SYTO-9/BC probe stained samples were chosen to quantify fluorescence intensity of red and green pixels. Using the software, the fluorescence intensity ratio (FIR) of bound LPS/bacterial cell was calculated. This ratio of fluorescence intensity indicates the relative amount of bound (neutralized) LPS per unit of bacteria, and the efficacy of an agent in reducing the biofilm’s toxicity. The greater the fluorescence intensity ratio, the higher LPS endotoxin neutralization efficacy. Ca:EPS; The Fluo-3™/Con-A™ stained specimens, both fluorescence channels were chosen to quantify fluorescence intensity ratio of green pixels (Calcium) to red pixels (EPS) and Con-A™ fluorescence channel was chosen to measure the biofilm thickness. Whereby, six selected fields of Con-A™ fluorescence channel of each specimen were evaluated. These fields were considered as representative of the whole sample after the observer’s general examination. The distance was measured from the surface of the biofilm to its base, measuring the thickness of the field, and subsequently the mean thickness of the biofilm of the corresponding specimen was calculated.

TABLE 2

LPS Neutralization, Sn Penetration, and EPS Thickness

| | Product | Glycine (% w/w) | Ratio Ca/EPS | EPS Thickness (μm) | Sn Penetration (%) | LPS Neutralization (%) |
|---|---|---|---|---|---|---|
| Ex. 1 | PBS | 0 | 1.2 | 28.66 | 5.30 | 21 |
| Ex. 2 | Hops/$SnCl_2$/$CaCO_3$ | 0 | 0.67 | 17.57 | 75.70 | 63 |
| Ex. 3 | Hops/$SnCl_2$/$CaCO_3$ + Glycine | 2 | 0.45 | 9.43 | 86.86 | 78 |
| Ex. 4 | Hops/$SnCl_2$/$CaCO_3$ + Glycine | 4 | 1.62 | 6.15 | — | — |

TABLE 2 shows the benefits of adding a suitable amino acid, such as glycine, to increase LPS neutralization and Sn penetration. Ex. 1, as shown in TABLE 1, is a control composition that includes varies chloride and phosphate salts. The use of Ex. 1 led to a final EPS thickness of 28.66 μm, a Sn penetration of 5.30%, and a LPS neutralization of 21%. Ex. 2 is a toothpaste composition, as shown in TABLE 1, with hops beta aid, stannous chloride, and calcium carbonate. The use of Ex. 2 led to a final EPS thickness of 17.57 μm, a Sn penetration of 75.70%, and a LPS neutralization of 63%. Ex. 3 is a toothpaste composition, as shown in TABLE 1, with hops beta aid, stannous chloride, calcium carbonate, and glycine at 2 wt %. Unexpectedly, the addition of 2% glycine led to a final EPS thickness of 9.43 lam, a Sn penetration of 86.86%, and a LPS neutralization of 78%. In other words, the addition of 2 wt % of glycine led to a 15% improvement in Sn penetration, a 25% improvement in LPS neutralization, and reduced the biofilm EPS matrix by 46%. The addition of glycine at 4%, as in Ex. 4, led to a final EPS thickness of 6.15 μm, which was a 65% reducing in the EPS thickness relative to the toothpaste in Ex. 2 (i.e. with no glycine).

Suitable oral care compositions can have a tin ion penetration of at least 75%, at least 80%, or at least 85%. Additionally, suitable oral care composition can have a LPS neutralization of at least 50%, at least 55%, at least 60%, at least 65%, at least 70%, or at least 75%. Additionally, suitable oral care compositions include those composition that can lead to a reduction of the biofilm EPS matrix thickness of at least 45%, at least 50%, at least 55%, at least 60%, or or at least 65% relative to an equivalent oral care composition without amino acid.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:

(a) about 0.01% to about 10%, by weight of the composition, of hops beta acid, wherein the hops beta acid is free of hydrogenated hops beta acid;

(b) about 0.01% to about 10%, by weight of the composition, of glycine;

(c) a tin ion source; and (d) 10% to 50% of an abrasive comprising calcium, wherein the dentifrice composition has an LPS neutralization of at least about 60%.

2. The dentifrice composition of claim 1, further comprising from about 0.01% to about 10%, by weight of the dentifrice composition, of a fluoride ion source.

3. The dentifrice composition of claim 2, wherein the fluoride ion source comprises sodium fluoride, stannous fluoride, amine fluoride, sodium monofluorophosphate, or combinations thereof.

4. The dentifrice composition of claim 1, wherein the dentifrice composition is essentially free of fluoride.

5. The dentifrice composition of claim 1, wherein the abrasive comprises calcium carbonate.

6. The dentifrice composition of claim 1, wherein the hops beta acid comprises lupulone, colupulone, adlupulone, or combinations thereof.

7. The dentifrice composition of claim 1, further comprising from about 0.01% to about 10%, by weight of the composition, of an antibacterial agent.

8. The dentifrice composition of claim 7, wherein the antibacterial agent comprises a metal ion source.

9. The dentifrice composition of claim 8, wherein the metal ion source comprises zinc.

10. The dentifrice composition of claim 1, wherein the tin ion source comprises stannous fluoride, stannous chloride, or a combination thereof.

11. The dentifrice composition of claim 1, further comprising an amino acid selected from a basic amino acid, an acidic amino acid, a neutral amino acid, and combinations thereof.

12. The dentifrice compositions of claim 11, wherein the amino acid comprises alanine, valine, isoleucine, tryptophan, phenylalanine, proline, methionine, leucine, serine, threonine, tyrosine, asparagine, glutamine, cysteine, citrulline, aspartic acid, glutamic acid, lysine, arginine, histidine, or a combination thereof.

13. The dentifrice composition of claim 1, wherein the hops beta acid comprises an extract of *Humulus lupulus*, the extract comprising less than 1%, by weight of the extract, of hops alpha acid.

14. The dentifrice composition of claim 13, wherein the extract comprises less than 5%, by weight of the extract, of hops oils.

15. The oral care composition of claim 1, wherein a reduction of biofilm thickness is at least 45% relative to an equivalent oral care composition without glycine.

16. A method of disrupting a dental biofilm in an oral cavity of a patient comprising:

applying the dentifrice composition of claim 1 to the dental biofilm.

17. The method of claim 16, wherein the dental biofilm has a thickness reduction of at least 60% after application of the dentifrice composition.

18. The method of claim 16, wherein the dental biofilm has a thickness reduction of at least 75% after application of the dentifrice composition.

19. The dentifrice composition of claim 5, wherein the abrasive is present at about 20% to about 50%.

20. The dentifrice composition of claim 19, wherein the abrasive is free of silica.

* * * * *